United States Patent [19]

Shultz et al.

[11] Patent Number: 5,580,747
[45] Date of Patent: Dec. 3, 1996

[54] NON-RADIOACTIVE ENZYME ASSAY

[75] Inventors: John W. Shultz, Verona; Douglas H. White, Madison, both of Wis.

[73] Assignee: Promega Corporation, Madison, Wis.

[21] Appl. No.: 185,448

[22] Filed: Jan. 21, 1994

Related U.S. Application Data

[63] Continuation-in-part of Ser. No. 791,928, Nov. 12, 1991, abandoned.

[51] Int. Cl.$^6$ .............................. C12Q 1/37; C12Q 1/50; G01N 31/00; A61K 38/00
[52] U.S. Cl. ............................... 435/24; 435/23; 435/17; 435/15; 435/18; 435/4; 435/21; 435/16; 435/810; 435/975; 436/2; 436/12; 436/13; 436/14; 436/15; 436/16; 436/17; 436/63; 436/74; 436/172; 436/800; 530/300
[58] Field of Search .................................. 435/24, 18, 4, 435/23, 21, 15, 16, 17, 810, 975; 436/2, 12, 13, 14, 15, 16, 17, 63, 74, 172, 800; 530/300, 328

[56] References Cited

U.S. PATENT DOCUMENTS

| | | | |
|---|---|---|---|
| 4,016,258 | 8/1975 | Said et al. | 435/24 |
| 4,681,842 | 7/1987 | Rosalki | 435/21 |
| 4,687,732 | 8/1987 | Ward et al. | 435/21 |
| 4,803,157 | 2/1989 | Sundberg et al. | 435/21 |
| 4,912,033 | 3/1990 | Ladenson et al. | 435/7 |
| 5,120,644 | 6/1992 | Ikenaka et al. | 435/15 |
| 5,242,801 | 9/1993 | Campbell et al. | 435/24 |

FOREIGN PATENT DOCUMENTS 059549 3/1989 Japan.

OTHER PUBLICATIONS

Dattagupta et al; Chem Abstract 104(5): 31369x (1985).
Kumar et al; Chem Abstract 108(19): 164220w (1988).
Stammer, C. H.; Abstract, Sequence of Cyclopropyl Peptide with Anti-Hyperten (1988).

Bowen, Heather J., William J. Enright, Kenji D. Nakamura, 1990, "Synthetic Peptide Substrate Assay for Protein Tyrosine Kinases". *Focus* 12, 4:105–07.

Bramson, H. Neal, Nancy Thomas, William F. DeGrado, E. T. Kaiser, 1980, "Development of a Convenient Spectrophotometric Assay for Peptide Phosphorylation Catalyzed by Adenosine 3', 5'-Monophosphate Dependent Protein Kinase", *J. Am. Chem. Soc.* 102:7156–7157.

Cook, Paul F., Maynard E. Neville Jr., Kent E. Vrana, F. Thomas Hartl, Robert Roskoski Jr., 1982, "Adenosine Cyclic 3', 5'-Monophosphate Dependent Protein Kinase: Kinetic Mechanism for the Bovine Skeletal Muscle Catalytic Subunit", *Biochemistry* 21:5794–5799.

House, Colin, Richard E. H. Wettenhall, Bruce E. Kemp, 1987, "The Infuence of Basic Residues on the Substrate Specificity of Protein Kinase C". *J. Biol. Chem.* 262:772–77.

Kemp, Bruce E. and Richard B. Pearson, 1990, "Protein Kinase Recognition Sequence Motifs", TIBS 15:342–346.

Kennelly, Peter J. and Edwin G. Krebs, 1991, "Consensus Sequences as Substrate Specificity Determinants for Protein Kinases and Protein Phosphatases". *J. Biol. Chem.*, 266:15555–15558.

(List continued on next page.)

*Primary Examiner*—John Kight
*Assistant Examiner*—Louise N. Leary
*Attorney, Agent, or Firm*—DeWitt Ross & Stevens SC

[57] ABSTRACT

The present invention is directed to the assay and purification of proteins, and particularly to the non-radioactive assay and purification of protein kinases, phosphatases and protease by incubating the enzyme with a substrate modified peptide to form a product modified peptide under conditions where the enzyme is active. The product modified peptide and substrate modified peptide are then separated, and the product modified peptide is measured. The present invention is also directed to kits and bioreagents for performing the assays.

26 Claims, 10 Drawing Sheets

OTHER PUBLICATIONS

McMurry, John, 1989, *Essentials of General, Organic, and Biological Chemistry*, Chapter 16: "The Molecules of Life: Enzymes, Vitamins, and Hormones", Prentice–Hall, Inc., New Jersey, pp. 339–359.

Owen, Whyte G., Charles T. Esmon and Craig M. Jackson, 1974, *J. Biol. Chem.*, 249:594–605.

Pearson, Richard B., James R. Woodgett, Philip Cohen, and Bruce E. Kemp, 1985, "Substrate Specificity of a Multifunctional Calmodulin–dependent Protein Kinase". *J. Biol. Chem.* 260:14471–14476.

Robyt, John F. and Bernard J. White, 1990, *Biochemical Techniques–Theory and Practice*, Waveland Press, Inc., Prospect Heights, IL, pp. 291–320.

Roskoski, Robert, Jr., 1983, "Assays of Protein Kinase". *Methods in Enzymology*, 99:3–6.

Seng, Thomas, Teresa C. M. Eames and David G. Osterman, 1991, "An HPLC Assay for Protein Kinase Activity Using Fluorescence Detection of Dansyl Peptide Substrates", (Abst.) *The Protein Society: Fifth Symposium*, Baltimore, MD, Jun. 22–26, 1991, p. 73.

Walton, Gordon M., Paul J. Bertics, Laurie G. Hudson, Thomas S. Vedvick and Gordon N. Gill, 1987, "A Three–Step Purification Procedure for Protein Kinase C: Characterization of the Purified Enzyme". *Anal. Biochem.* 161:425–437.

Casnellie, John E., 1991, "Assay of Protein Kinases Using Peptides with Basic Residues for Phosphocellulose Binding". *Methods in Enzymology* 200:115–120.

Glover, Clairborne V. C. and C. David Allis, 1991, "Enzyme Activity Dot Blots for Assaying Protein Kinases". *Methods in Enzymology* 200:85–90.

Kemp, Bruce E. and Richard B. Pearson, 1991, "Design and Use of Peptide Substrates for Protein Kinases". *Methods in Enzymology* 200:121–134.

Malencik, Dean A. and Sonia R. Anderson, 1983, "Characterization of a Fluorescent Substrate for the Adenosine 3', 5'–Cyclic Monophosphate–Dependent Protein Kinase". *Anal. Biochem.* 132:34–40.

Racker, Efraim, 1991, "Use of Synthetic Amino Acid Polymers for Assay of Protein–Tyrosine and Protein–Serine Kinases". Methods in Enzymology 200:107–111.

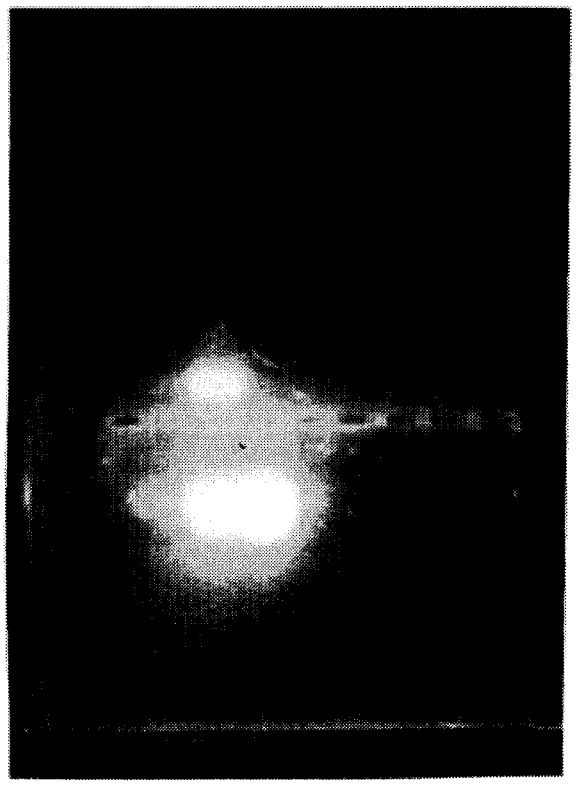
LANES 1 2 3 4
FIG. 5
FIG. 6
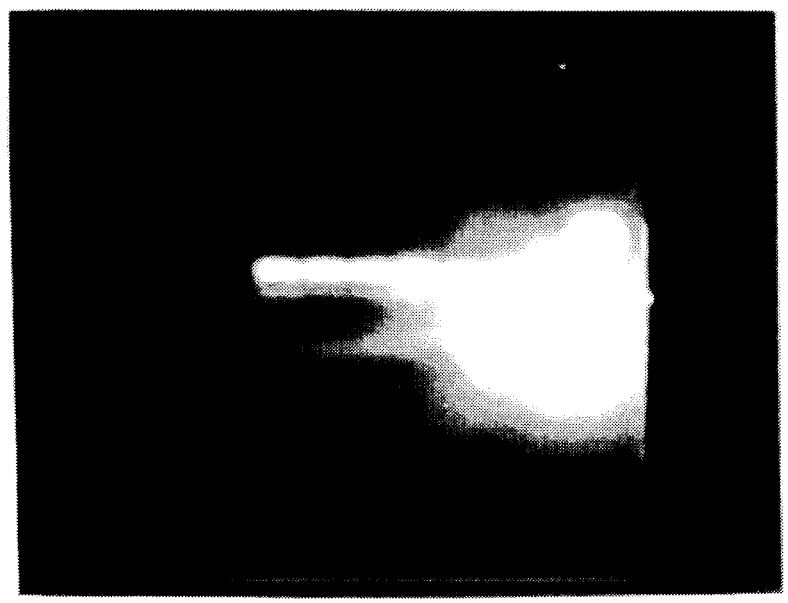
+ LANES 1 2 3 4 5 6 7 8

LANES  1  2  3  4  5  6  7  8

LANES  1  2  3  4  5  6

LANES  1 3 5 7 9 11 13 15 17
       2 4 6 8 10 12 14 16 18

LANES  1 2 3 4 5 6 7 8 9 10 11 12 13 14 15 16 17

LANES  1 2 3 4 5 6 7

LANES  1 2 3 4 5 6 7 8 9 10 11 12 13 14

LANES 1 2 3 4 5

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /label=LABEL
            / note="LOCATION OF DANSYL DETECTION TAG"

( x i ) SEQUENCE DESCRIPTION: SEQ ID NO:1:

Leu  Arg  Arg  Ala  Ser  Leu  Gly
    1                       5

( 2 ) INFORMATION FOR SEQ ID NO:2:

( i ) SEQUENCE CHARACTERISTICS:
        ( A ) LENGTH: 7 amino acids
        ( B ) TYPE: amino acid (D) TOPOLOGY: linear (ii) MOLECULE TYPE: peptide (ix) FEATURE:
    (A) NAME/KEY: Binding-site
    (B) LOCATION: 1
    (D) OTHER INFORMATION: /label=LABEL
        / note="LOCATION OF DANSYL DETECTION TAG"

(xi) SEQUENCE DESCRIPTION: SEQ ID NO:2:

```
Leu Arg Arg Ala Ser Val Ala
1               5
```

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 1
        (D) OTHER INFORMATION: /label=LABEL
            / note="LOCATION OF SULFORHODAMINE 101 DETECTION TAG"

(xi) SEQUENCE DESCRIPTION: SEQ ID NO:3:

```
Leu Arg Arg Ala Ser Val Ala
1               5
```

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 1
        (D) OTHER INFORMATION: /label=LABEL
            / note="LOCATION OF LISSAMINE RHODAMINE DETECTION TAG"

(xi) SEQUENCE DESCRIPTION: SEQ ID NO:4:

```
Arg Phe Ala Arg Lys Gly Ser Leu Arg Gln Lys Asn Val
1               5                           10
```

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 1
        (D) OTHER INFORMATION: /label=LABEL
            / note="LOCATION OF LISSAMINE RHODAMINE DETECTION TAG"

(xi) SEQUENCE DESCRIPTION: SEQ ID NO:5:

```
Gln Arg Arg Gln Arg Lys Ser Arg Arg Thr Ile
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /label=LABEL
            / note="LOCATION OF LISSAMINE RHODAMINE
            DETECTION TAG"

( x i ) SEQUENCE DESCRIPTION: SEQ ID NO:6:

```
Pro Leu Ser Arg Thr Leu Ser Val Ala Ala Lys Lys
1               5                   10
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /label=LABEL
            / note="LOCATION OF LISSAMINE RHODAMINE
            DETECTION TAG"

( x i ) SEQUENCE DESCRIPTION: SEQ ID NO:7:

```
Leu Arg Arg Ala Ser Leu Gly
1               5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /label=LABEL
            / note="LOCATION OF LISSAMINE RHODAMINE
            DETECTION TAG"

( x i ) SEQUENCE DESCRIPTION: SEQ ID NO:8:

```
Asp Arg Val Tyr Ile His Pro Phe
1               5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site (B) LOCATION: 1
(D) OTHER INFORMATION: /label=LABEL
    / note="LOCATION OF LISSAMINE RHODAMINE DETECTION TAG"

(xi) SEQUENCE DESCRIPTION: SEQ ID NO:9:

Arg Ser Leu Asn Tyr Pro Gln Ser Trp
1               5

(2) INFORMATION FOR SEQ ID NO:10:

(i) SEQUENCE CHARACTERISTICS:
    (A) LENGTH: 10 amino acids
    (B) TYPE: amino acid
    (D) TOPOLOGY: linear (ii) MOLECULE TYPE: peptide (ix) FEATURE:
    (A) NAME/KEY: Binding-site
    (B) LOCATION: 1
    (D) OTHER INFORMATION: /label=LABEL
        / note="LOCATION OF LISSAMINE RHODAMINE DETECTION TAG"

(xi) SEQUENCE DESCRIPTION: SEQ ID NO:10:

Ala Thr Leu Asn Phe Pro Ile Ser Pro Trp
1               5                   10

(2) INFORMATION FOR SEQ ID NO:11:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (ix) FEATURE:
    (A) NAME/KEY: Binding-site
    (B) LOCATION: 1
    (D) OTHER INFORMATION: /label=LABEL
        / note="LOCATION OF LISSAMINE RHODAMINE DETECTION TAG"

(xi) SEQUENCE DESCRIPTION: SEQ ID NO:11:

Pro Leu Ser Arg Thr Leu Ser Val Ala Ala Lys
1               5                       10

NON-RADIOACTIVE ENZYME ASSAY

REFERENCE TO RELATED APPLICATION

This is a continuation-in-part of U.S. Ser. No. 07/791,928, filed on Nov. 12, 1991, now abandoned, in the names of John W. Shultz and Douglas H. White entitled "Non-Radioactive Enzyme Assay," which application is incorporated herein by reference.

FIELD OF THE INVENTION

The present invention relates generally to protein assays. More specifically, the invention relates to assays of enzymes. The present invention relates particularly to a non-radioactive method of assaying the activity of protein kinases, phosphatases and proteases.

REFERENCE TO CITED ART

Reference is made to the section preceding the claims for a full bibliography citation of the art cited herein.

DESCRIPTION OF THE PRIOR ART

Enzymes are large proteins that catalyze reactions in living cells. As used in this discussion, the term "catalyze" refers to a substance that increases the velocity of a reaction over the velocity of an uncatalyzed reaction without itself undergoing a change. Enzymes are specific in their reactions. An individual enzyme may catalyze the reaction of one substrate or of a group of related substrates.

In healthy persons, most enzymes are found within cells. Some diseases, however, release enzymes from dying cells into the blood. The increased levels of enzymes can then be measured. An abnormal level of enzymes in the blood characterizes certain medical conditions. For example, an enzyme assay for abnormal levels of creatine kinase in the blood is useful as a diagnostic of heart disease. When a heart attack occurs, cells are damaged and their enzymes leak into the bloodstream. Enzyme levels increase markedly immediately following a heart attack. Therefore, a confirmation of a heart attack can be made by analyzing the enzyme levels in the blood. In like manner, bone or liver diseases can be diagnosed by increased levels of alkaline phosphatase in the blood stream. Prostate cancer is diagnosed by increased levels of acid phosphatase. Reference is made to McMurry (1989) for a general description of the medical uses of enzymes.

Enzymes are classified into groups according to the general kind of reaction they catalyze. For purposes of the present invention, reference is specifically made to two of the groups: (1) Transferases, which catalyze the transfer of a group from one substrate to another; and (2) Hydrolases, which catalyze the hydrolysis, i.e., the breakdown of proteins to amino acids, of substrates. The present invention is specifically directed to the transferase subgroups kinases and phosphatases, and the hydrolase subgroup proteases.

Kinases

Protein kinases are enzymes which covalently modify proteins and peptides by the attachment of a phosphate group to one or more sites on the protein. Many of the known protein kinases use adenosine triphosphate (ATP) as the phosphate donor and place the gamma phosphate from this molecule onto a histidine (His or H), tyrosine (Tyr or Y), serine (Ser or S) or threonine (Thr or T) residue in the protein. The location of the site of modification and the type of residue modified by the kinases is determined by the specific kinase under study.

Studies have shown kinases to be key regulators of many cell functions, including signal transduction (Ullrich and Schlessinger, 1990), transcriptional regulation (Pawson and Bernstein, 1990), cell motility (Miglietta and Nelson, 1988), and cell division (Pines and Hunter, 1990). Several oncogenes, such as raf and src, have been shown to encode protein kinases (Bellas et al., 1991), suggesting that kinases play a role in oncogenesis. Indeed few, if any, physiological processes exist in eukaryotes that are not dependent on phosphorylation. It has been postulated that the total number of protein kinases encoded in the mammalian genome alone could number in the thousands (Hunter, 1987). Due to their physiological relevance, variety, and ubiquitousness, protein kinases have become one of the most important and widely studied family of proteins in biochemical and medical research.

Protein kinases are often divided into two groups based on the amino acid residue they phosphorylate. The Ser/Thr kinases include cyclic AMP- (cAMP-) and cGMP-dependent protein kinases, calcium- and phospholipid-dependent protein kinase C, calmodulin dependent protein kinases, casein kinases, cell division cycle (CDC) protein kinases, and others. These kinases are usually cytoplasmic or associated with the particulate fractions of cells, possibly by anchoring proteins (Carr et al., 1991).

The second group of kinases, which phosphorylate Tyr residues, are present in much smaller quantities, but play an equally important role in cell regulation. These kinases include several receptors for molecules such as growth factors and hormones, including epidermal growth factor receptor, insulin receptor, platelet-derived growth factor receptor, and others. Structure-function studies have indicated that many Tyr kinases are transmembrane proteins (Todderud and Carpenter, 1989), with their receptor domains located on the outside of the cell and their kinase domains on the inside.

Recent studies in yeast have proven the existence of a protein kinase that phosphorylate His residues on substrate proteins. The significance of this N-linked phosphorylation has yet to be explored (Matthews et al., 1991).

Phssphatases

Protein phosphatases are enzymes that catalyze the removal of phosphate moieties from proteins which contain such modifications. The sites which can be dephosphorylated is dependent upon the specific enzyme under study. Four major types of protein phosphatases have been identified, which have been grouped into two classes: type 1 protein phosphatase (protein phosphatase-1 or PP1) and type 2 protein phosphatases (PP2A, PP2B, and PP2C). The classes are distinguished by their substrate specificity and dependence on other molecules for activation.

As with kinases, both Ser/Thr and Tyr phosphatases have been found. Peptide substrates for individual protein phosphatases have been investigated and identified (Kennelly and Krebs, 1991).

Proteases

Proteases have also been found to be important in many biological processes. Some of these processes, such as the formation of a fibrin clot, which begins the healing process for wounds, involve many different proteases acting in concert. When these proteases do not act as they should, the results can be devastating. The many forms of hemophilia are the result of mutations in proteases. In performing research on the role of proteases on cellular function, it is essential to accurately and rapidly determine the amount of active protease present in samples. For a general discussion on these enzymes in such process, reference is made to Neurath (1989), which reference is incorporated herein by reference.

Activity Determination

Reference is made Robyt and White (1990) for a general description of methods for determining the activity of an enzyme. Robyt and white define the activity of an enzyme as the amount of reaction that a certain amount of enzyme will produce in a specified period of time. The activity is determined by measuring the amount of product produced or the amount of substrate used up per unit of time under high concentrations or saturating conditions of substrate. This is usually accomplished by performing a chemical analysis for the product or substrate.

Radioactive Detection of Activity

Most current methods of measuring protein kinase activity are based on the radioactive detection method described by Roskoski (1983). In this method, a sample containing the kinase of interest is incubated with activators and a substrate in the presence of gamma $^{32}$P-ATP. Often, a general and inexpensive substrate, such as histone or casein, is used. After a suitable incubation period, the reaction is stopped and an aliquot of the reaction mixture is placed directly onto a filter which binds the substrate. The filter is then washed several times to remove excess radioactivity, and the amount of radiolabelled phosphate incorporated into the substrate is measured by scintillation counting (Roskoski, 1983). This method is widely used and provides an accurate method for determining protein kinase activity in both crude and purified samples.

The use of $^{32}$P in the assay poses significant disadvantages. A major problem is the disposal of the radionuclide. For sensitive detection, relatively high quantities of $^{32}$P must be used routinely and subsequently disposed. The amount of liquid generated from the washings is not small, and contains $^{32}$P. Due to government restrictions, this waste cannot be disposed easily. It must be allowed to decay, usually for at least six months, before disposal. Another disadvantage is the hazard of working with the isotope. Shielding, special waste containers and caution are necessary for safe handling and pose great inconvenience and potential danger to workers. The half life of $^{32}$P also provides a problem: with the half life of two weeks, the labelled ATP must be replaced often. Also, restrictions on the use of radioactivity, especially overseas, make the use of $^{32}$P labelled ATP cumbersome. Further still, the lower detection limit of the assay is determined by the level of background phosphorylation and is therefore variable. In short, the study of protein kinases would be greatly facilitated by the development of an efficient and accurate assay that does not require the use of radioactivity.

Although as ubiquitous and as important in cellular regulation as protein kinases, protein phosphatases are not studied as extensively. This is partially due to the difficulty in assaying the enzymes. Protein phosphatase assays contain the same difficulties as assays of protein kinases, with further complications. Assays of protein phosphatases require radioactively labelled phosphorylated substrates, which must be created specifically for this task. These substrates decay rapidly and are hazardous to work with. Most assays of phosphatase activity are measured by the removal of a label from the substrate. The increased difficulty in these assays is due to the fact that the substrate protein or peptide has a limited shelf life, and the isotope has a half life of two weeks. After labelling, the peptide is incubated with the phosphatase, and the resulting decrease in labelled peptide is measured by conventional means.

A non-radioactive method to measure protein phosphatase activity, perhaps using stable phosphorylated peptide substrates, would greatly aid research in this area. By providing non-radioactive substrates that can be easily quantitated after dephosphorylation, the researcher avoids the difficulties inherent with using $^{32}$P; the non-radioactive substrates are also stable for long periods of time, avoiding the problems involved with radioactive decay.

Non-Radioactive Detection of Activity Dot Blot

A non-radioactive method of detecting kinase activity has been developed in which tyrosine phosphorylation is detected by using anti-phosphotyrosine antibodies (Rijksen et al., 1989). After incubation of the tyrosine kinase with unlabelled ATP and a suitable substrate, the reaction mixture is subjected to a dot blot assay on a PVDF membrane. The extent of phosphorylation is determined by reaction with antiphosphotyrosine antibody, followed by detection with an immunogold staining procedure. The amount of phosphotyrosine present is detected with a densitometer. Aside from the absence of radioactivity, this method has the advantage of low background. Because phosphoserine is not detected, the sensitivity of the detection is increased.

The main disadvantage of the dot blot method is that it is limited to detecting Tyr kinases. Antibodies to phosphotyrosine can be produced due to the size of the antigen. Attempts to produce similar antibodies to phosphoserine and phosphothreonine have not been successful. In addition, the assay requires several incubation and washing steps, each of a considerable length, which results in a long assay time. Finally, the result of the assay is a colored dot on the blot which limits the effective sample range of the assay and requires that the user quantitate the final result by use of a scanning densitometer, a piece of equipment not available in all laboratories. The densitometer must have beam dimensions covering at least the targeted cross section of the dots generated.

Spectrophotometric Assay

Use of a modified substrate allows spectrophotometric detection of kinase activity. In this application, the cAMP-dependent protein kinase substrate Kemptide (Bramson et al., 1980) is modified by placing a (o-NO$_2$)-tyrosine residue on the N-terminal side of the phosphorylated serine. This modification does not interfere with the ability of the peptide to be a substrate, and causes phosphorylation to alter the absorbance of the peptide at 430 nm. This allows continual measurement of kinase activity, whereas measurement by radionuclide requires removal of an aliquot of the reaction before phosphate incorporation could be measured.

Unfortunately, the spectrophotometric assay requires large amounts of substrate as well as kinase to determine activity effectively. While useful for mechanistic studies requiring a continuous measurement of phosphorylation, this method may not be useful when limited amounts of kinase are available or when the researcher must screen a large number of samples for relative kinase activity. In addition, specific peptides are needed for every protein kinase and it is not known if (1) such modifications will be tolerated by all kinases and (2) if these changes will alter the specificity of phosphorylation for a peptide by a particular kinase.

Other spectrophotometric assays for kinase activity have been developed using coupled reactions. The conversion of phosphoenolpyruvate to pyruvate can occur in the presence of ADP generated by kinase phosphotransfer and pyruvate kinase (Cook et al., 1982). The pyruvate is then converted to lactate by lactate dehydrogenase and detected by reading the absorbance at 340 nm. While effective, the method does have disadvantages: in crude samples, any ATPase activity will increase the background and the intrinsic oxidoreductive reactions present in such extracts will interfere with activity measurements. In addition, the assay is not very sensitive.

Fluorescence Assay

Another non-radioactive detection method for kinase activity involves a change in fluorescence upon substrate phosphorylation. The substrate Malantide, a tetradecapeptide derived from the phosphorylation site of the β-subunit of phosphorylase kinase, is an effective substrate for cAMP-dependent protein kinase, and exhibits a decrease in fluorescence upon phosphorylation. Like the spectrophotometric assay, it allows continual measurement of kinase activity. However, it uses large amounts of synthetically prepared peptide, and it requires access to a fluorometer.

Another type of assay is useful for cAMP dependent protein kinase by use of a fluorescently labeled peptide. The measurement of activity depends upon the separation of the non-phosphorylated and phosphorylated forms of the peptide by use of high pressure liquid chromatography (HPLC) (Seng et al., 1991). While this assay does not require the use of radioactivity, it is cumbersome in that each sample has to be individually injected and analyzed, thus requiring more time for the assay of several samples than would be possible using standard radioactive assays. Again, quantitation of the products of the assay is performed using fluorescent measurement of the amount of peptide altered. Fluorometers are not commonly available in many laboratories. Additionally, the assay may not be functional in crude enzyme preparations. Because most of the assays measuring protein kinases are performed on crude samples and because it is not known if the peptide would be degraded in crude peptide mixtures, the ultimate utility of this assay is questionable.

U.S. Pat. No. 5,120,644 to Ikenaka et al. disclose a method for the measurement of enzymatic activities using modified peptide substrates. Their method employs peptides which have been modified by the addition of a fluorescent group. They describe separation of the substrate peptide from the product peptide by high performance liquid chromatography, hydrophobic chromatography either in normal or reverse phase, gel filtration chromatography, ion exchange chromatography, and affinity chromatography with high performance liquid chromatography cited as their method of choice. Unfortunately, each of these methods is not useful for separating multiple samples at one time, as each sample must be applied to the separation matrix and fractionated individually. This has two drawbacks for the researcher: the researcher must take additional time for the separation as each must be separated individually; and the method requires the researcher to have chromatographic equipment for the separation of the materials. The cost of this equipment results in increased expenses for the end user.

Protease Assays

Proteases are mainly assayed in two different ways: by digestion of specific substrates which allow the researcher to directly monitor the activity of the enzyme or, by digestion of a relatively nonspecific substrate which can allow the activity of general proteolytic activity to be measured. For a general treatise on protease assays, reference is made to Sarath et al. (1989), which is incorporated herein by reference.

Proteases have also been assayed by cleavage of large proteins such as casein and hemoglobin. When such assays are performed, either the amount of hydrolysis is followed by measuring the release of free protons generated by the new carboxyl group formed in the reaction or by measurement of the amount of trichloroacetic acid (TCA) soluble peptide generated from the substrate using a variety of reagents such as Folins reagent (Sigma Chemical Corp., St. Louis Mo.). In addition, some large substrates such as azocasine have been chemically modified to produce a substrate molecule with colored dyes attached. Proteases can be assayed using such substrates by measurement of the TCA soluble peptide generated by digestion of the substrate by the protease. Such assays are undesirable as they do not distinguish between different proteolytic activities. Also the solubility of such substrates, coupled with the low detectability of the dyes bound to the substrate, often results in an assay with very poor sensitivity.

An additional protease assay has been reported which utilizes a substrate which has several fluorescent tags attached to one substrate. The fluorescent tags quench the emission of light from the return of any one tag to the ground state due to the close proximity of the dyes in space. Proteolytic cleavage of the substrate by proteases allows the segments of the peptide carrying these labels to diffuse apart from each other, thus increasing the fluorescence of the solution carrying the substrate and allowing the activity of the protease to be measured. This type of assay, however, requires that the substrate be soluble when it contains several such tags and these tags have been known to cause insolubility of peptides containing such modifications. In addition, such an assay will not be helpful in defining the cleavage site within the peptide—thus allowing determination of the specificity of the protease—for any cleavage will generate the same signal.

If the technology currently used to study protein kinases, phosphatases and proteases could be improved, knowledge of their function in metabolism would be increased. One technique used to study almost all areas of research involves the accurate and sensitive detection of the enzyme activity. Assays for specific kinases, phosphatases and proteases are used in many applications, from purification to mass screening of potential inhibitors. Improvements in the sensitivity, selectivity, and rapidity of the assays would greatly aid in their study.

SUMMARY OF THE INVENTION

The present invention is directed to a non-radioactive enzyme assay which overcomes the deficiencies discussed above. The assay can be performed rapidly and at great sensitivity in both purified systems and in crude samples of the enzyme. The method allows the assay to be performed using commonly available equipment to yield accurate results. The assay is generally directed to the detection of protein kinases, phosphatases and proteases.

The invention is specifically directed to a non-radioactive method of quantitating the activities of specific protein kinases, phosphatases and proteases on a peptide substrate by measuring the amount of the specific peptide substrate that has been reacted by the enzyme under assay. Preferred steps include incubating the enzyme with the substrate modified peptide to form a mixture of substrate modified peptide and product modified peptide under conditions where the enzyme is active. The substrate modified peptide and product modified peptide are then separated by electrophosresis. The amount of the product modified peptide that has been formed by the enzyme under assay can then be measured.

The present invention is also directed towards the assay of enzymes using substrate modified peptides described in the invention. The use of these peptides are advantageous in that they not only allow determination of the activity of the protease, but also can be helpful in confirming the specificity and purity of the enzymes by generating sets of unique fragments from the substrate modified peptide which are characteristic of the type of proteolytic activity present in the sample.

The present invention is also directed to a bioreagent for quantitating the presence or activity of an enzyme, such as protein kinase, phosphatase or protease. The bioreagent is selected from the following group of peptides: Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 9 (SEQ ID NO:9), Promega Peptide 10 (SEQ ID NO:10), Promega Peptide 11 (SEQ ID NO:11) and analogs thereof.

The invention is also directed to kits for quantitating the activities of an enzyme selected from the group consisting of protein kinases and protein phosphatases or proteases using a substrate modified peptide. The kits include at least a substrate modified peptide modified by chemical reaction to allow easy visualization/quantitation of the substrate modified peptide and separation protocols for isolation of either the substrate modified peptide or product modified peptide.

The present invention is also directed towards a kit for performing protease assays, comprising a substrate or substrates for protease digestion made in accordance with the present invention and instructions on how to use the substrate for the assay of protease activity and preferably including protocols for the confirmation of the specificity of the protease under assay.

Surprisingly, a wide variety of peptide molecules which have been modified to allow their easy quantitation by a variety of means can be used as substrates for protein kinases, proteases and phosphatases. The measurement of the activity of these enzymes can be performed by separation of the product modified peptide and substrate modified peptide species using electrophoresis and quantitation of the amount of either the residual substrate modified peptide of the reaction, the product modified peptide of the reaction, or both.

The enzymes present in a sample of a body fluid, such as blood or lymph, can be measured within a very short period of time with high accuracy by the assay method of the present invention. The method includes incubating a sample of the body fluid containing at least one of the enzymes with the substrate modified peptide of the present invention under conditions where the enzyme will form a product modified peptide. By the use of the substrate modified peptide, the enzyme can easily be diagnosed in the body fluids and the appropriate disease can be diagnosed.

The results are unexpected for at least three reasons: (1) the enzymes have strict sequence requirements, and therefore might not be thought to recognize a peptide which has been modified chemically as a substrate; (2) the modification tags used, while known in the literature as species which allow quantitation of very small amounts of a modified chemical species, often result in the production of a modified species which has a very low solubility in solvents needed for activity of the enzymes under study; and (3) chemical species with polyaromatic, hydrophobic structures, as disclosed in the examples to follow, have been used to bind enzymes with nucleotide substrates such as ATP. Such binding inhibits the activity of the enzymes by preventing the entry of the substrate molecules, thus preventing assay of the enzymes in the presence of dyes.

Additionally, it was not known if the modified peptides of the invention could withstand degradation in complex samples, such as total cell lysates, where various proteases and other enzymes might destroy the peptides too rapidly to allow assay of other enzymes such as that of the protein kinases and phosphatases present.

In both pure and crude samples, the products of the invention have other unexpected advantages including the ability to assay the activity of an enzyme without measurement of other contaminating reactions which take place in the sample. For example, when protein kinases are measured in crude sample preparations using radioactive phosphate incorporated into added substrate and assay conditions well-known in the art, the activity of the assay actually measures the reaction of the enzyme with the substrate and the reaction of other kinases in the sample with protein and peptide substrates present in the sample. The present invention allows the measurement of only the modification of the specific peptide substrate added to the sample, thus avoiding the measurement of other activities in the sample.

Finally, it was unexpected that the resolution of small peptides fractionated by electrophoresis in agarose gels would be capable of allowing a precise separation and accurate quantitation of the substrate modified peptide from the product modified peptide. In the literature, some researchers have suggested methods for the fractionation of small peptides by electrophoresis in a gel matrix. However, these methods do not work for very small peptide species and the methods mask the electrophoretic properties of the peptide. Thus, these methods, even if they could fractionate peptides as small as 20 amino acids, would not be useful for the fractionation of peptides modified by the action of an enzyme in a manner that results in a change in the charge of the peptide.

However, separation using electrophoresis, particularly separations which utilize fractionation of the materials in an agarose matrix, provide several advantages to the researcher. Such separations commonly use gel systems which allow multiple samples to be fractionated at one time. In fact, it is not unusual to fractionate over 20 samples at one time using a single separation system, saving the user time that would be needed to individually separate each sample. Such systems also provide the following advantages: side-by-side comparisons of the mobilities of the fractionated species, allowing very small changes in the mobility of different species to be accurately determined; the separations, particularly if done in the absence of an ionic detergent, are dependent upon both the molecular mass and the intrinsic charge of the material to be separated; therefore, changes in a molecule, such as those which add or remove charges, group to a material (as exemplified by the addition or removal of phosphate and sulfate moieties) those which increase the molecular mass of the material (as exemplified by changes such as glycosidations and lipid modifications) and those which decrease the size of the material (as exemplified by the protolytic cleavages of the peptide) may be observed. The materials used to perform electrophoretic separations are commonly present in laboratories and the disposable materials used in the separations are very inexpensive. Thus, electrophoretic separations incur very little cost to the user. Even if the materials to perform such separations are purchased by the user, the expense is small compared to the costs required to perform other separation techniques such as high performance liquid chromatography.

BRIEF DESCRIPTION OF THE DRAWINGS

In the drawings:

FIG. 5 is a photograph illustrating the synthesis of Promega Peptide 3 (SEQ ID NO:3) (Sulforhodamine 101 derivative of $V^6A^5$ Kemptide) in Example 8.

FIG. 6 is a photograph illustrating the purification of Promega Peptide 3 (SEQ ID NO:3) in Example 9.

DETAILED DESCRIPTION OF THE INVENTION

Figure 1:
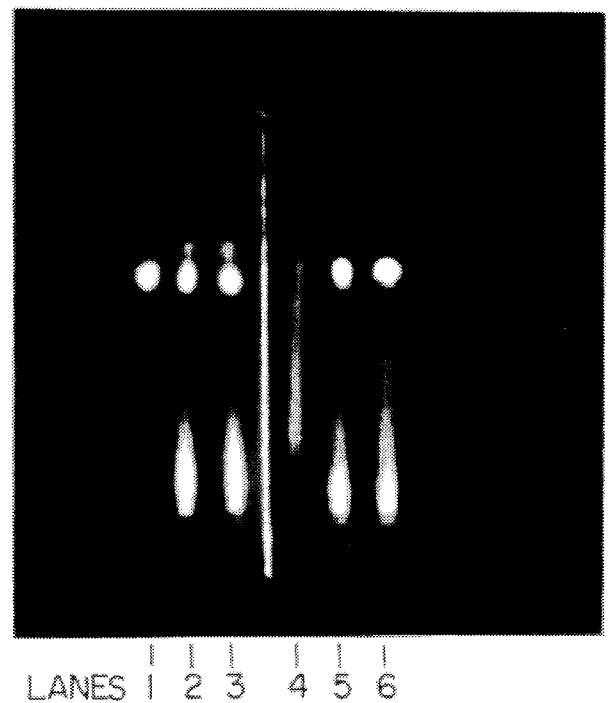
FIG. 1 is a photograph illustrating the separation of phosphorylated Promega Peptides 1 (SEQ ID NO:1) and 2 (SEQ ID NO:2) from the unphosphorylated peptides by thin layer chromatography in Example 4.

The present invention quantitates the activities of enzymes by measuring the amount of a specific modified peptide substrate that has been reacted by the enzyme under assay. Although the present invention is preferably directed to quantitating the enzymes protein kinase, phosphatase and protease, the invention has wider application. The present invention is contemplated to be used to assay phosphatases, kinases, proteases, methylases, de-methylases, glycosidases, and de-glycosidases and other enzymes.

For example, a coupled, modified peptide substrate having N-linked glycosidation on an Asn residue could be used to measure the activity of a de-glycosidase that removed N-linked glycosidation. The reaction would uncover a site for Endoprotease Asn N, which would otherwise be masked by the glucose residues.

In another example, a linked, modified peptide substrate having a Lys residue, which can be methylated by the methylases present in many cells, would mask this site for cleavage by proteases such as Endoprotease Lys-C. The activity of the enzymes which removes methyl residues from Lys residues can be measured by simply attaching a methylated peptide and measuring the amount of cleavable peptide that is generated.

Definitions

For purposes of the present invention, the following definitions will apply:

Activity of an Enzyme: The amount of reaction that a certain amount of enzyme will produce in a specified period of time.

Amino Acids: Amino acids are shown either by three letter or one letter abbreviations as follows:

| Abbreviated Designation | Amino Acid |
|---|---|
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

Complex Sample: A sample consisting of more than 10 individual protein components.

Crude Sample: An extract from an entire organism or tissue made by lysis of the tissue or organism under mild conditions and removal of particular material.

Modified peptide: A chemical species composed of a peptide as described below which has been subsequently reacted with a second chemical moiety which allows the peptide to be monitored by virtue of the properties of the second chemical moiety. This second chemical moiety will be referred to in this application as a detector segment or modification tag. It should be noted that such a modified peptide can consist in almost all cases of other chemical elements in addition to amino acids, such as those modifications described in the definition of peptides.

Peptide: A compound consisting of 2–30 naturally occurring or synthetic amino acids which can also be further modified, as described above, which is covalently linked through peptide bonds formed from the α-carboxyl group of one amino acid and the α-amino group of the next amino acid by elimination of a molecule of water. The amino acids can be either those naturally occurring amino acids described above, chemically synthesized variants of such amino acids such as norleucine, or modified forms of these amino acids which can be altered from their basic chemical structure by addition of other chemical groups which can be found to be covalently attached to them in naturally occurring compounds. Some of the modifications so attached include: phosphate groups, lipid groups, nucleotide groups, and polymers of sugars and will include other modifications known to those skilled in the art.

Phosphorylate: The addition of a phosphate group to a substrate.

Product modified peptide: A chemical species which is formed by the action of an enzyme on a substrate modified peptide, as described below, which has been altered from the original bonding pattern between the atoms of the substrate modified peptide. Such alterations can include the addition or removal of new chemical species to the substrate modified peptide. The particular changes made in the substrate modified peptide will depend upon the particular enzyme which has been involved in the alteration of the substrate modified peptide. Examples of such product modified peptides include but are not intended to be limited to: (a) a product modified peptide which had been formed by incubation of a modified peptide with a protein kinase under conditions where the enzyme has altered the substrate modified peptide by addition of a phosphate group to the peptide from a phosphate donor such as ATP; (b) a product modified peptide which had been formed by incubation of a substrate modified peptide with a protein phosphatase under conditions where the enzyme has altered the substrate modified peptide by removal of a phosphate group from the peptide; and (c) a product modified peptide formed by incubation of a substrate modified peptide with a protease under conditions where the protease breaks one or more of the peptide bonds in the substrate modified peptide, thus producing chemical species where the detector segment is present on a chemical species with a smaller molecular mass than that of the original peptide. It should be noted that the product modified peptide may be used as a substrate modified peptide in subsequent reactions; for example, a product modified peptide isolated from the incubation of a protein kinase with a substrate modified peptide which acquired a phosphate group covalently attached to the peptide may be used by as a substrate modified peptide for measurement of the activity of a protein phosphatase in a subsequent reaction.

Pure Sample: A sample of less than 10 proteins.

Quantitation: The ability to numerically determine a property.

Sequence requirements: The property of an enzyme to have the ability to recognize and catalyze a reaction on only a subset of peptides due to the peptide sequence of these substrates.

Substrate: The substance on which an enzyme acts.

Substrate modified peptide: A modified peptide which can be changed by the action of an enzyme such that an alteration in the bonding pattern between the atoms of the modified peptide takes place. Such changes can include the addition or removal of chemical species to the modified peptide. Often it will be desirable to design a particular substrate modified peptide for assay of a particular enzyme of interest. In such cases, it will be important to design such a substrate modified peptide such that it contains the recognition sequence of the enzyme within its structure; such as including a lysine or arginine not followed by a proline in a substrate designed for assay of the protease trypsin. A potential substrate modified peptide contains the particular site and form of an amino acid necessary for its functioning. For example, a potential substrate modified peptide for a protein phosphatase will have to contain a phosphorylated amino acid somewhere in its structure. A potential substrate modified peptide for a protein kinase will have to contain an amino acid which can act as a phosphate acceptor such as a serine. The utility of a potential substrate modified peptide for assay of a particular enzymatic activity can be determined by incubating the potential substrate modified peptide with the enzyme under conditions where the enzyme is known to be active and observing the rate with which product modified peptide is generated. In general, substrate modified peptides which can be converted to product modified peptides more rapidly will be considered better peptides for assay of the enzyme.

Enzymes

The present invention relates generally to the assay and purification of proteins, and specifically to enzymes, particularly to those proteins which modify proteins. The enzymes specifically described in this specification are kinases, phosphatases and proteases.

The enzymes measured by the assay techniques of the present invention have strict sequence requirements. As such, they might not be thought to recognize a peptide which has been modified chemically as a substrate.

A general description of the enzymes kinases, phosphatases and proteases is found in the prior art section of this patent application and is incorporated herein to describe the characteristics of these enzymes.

Kinases—The kinases quantified in the present study preferably use adenosine triphosphate (ATP) as the phosphate donor and place the gamma phosphate from this molecule onto a His, Tyr, Ser or Thr residue in the protein. Protein kinases are distinguished by their ability to phosphorylate substrates on discrete sequences. These sequences have been determined by sequencing the amino acids around the phosphorylation sites, and are usually distinct for each protein kinase (Kemp and Pearson, 1990). Some overlap in targets have been observed with certain kinases. It has been shown that several different kinases can phosphorylate a common protein on different sites, such as is seen with glycogen synthetase (Roach, 1990). This recognition sequence on the substrate gives the different kinases great specificity and allows them to control different aspects of regulatory pathways.

The substrate binding site on the kinase is believed to exist in the enzymes' catalytic domain. This domain is common to all protein kinases. It typically contains over 240 residues, and also contains the kinase's ATP binding site.

Phosphatases—Phosphatases derive from a group of enzymes known as hydrolases which hydrolytically cleave bonds with the consumption of water. Examples of phosphatases include alkaline and acidic phosphatases which hydrolyze phosphoric acid esters.

Proteases—Proteases are able to cleave the peptide bond linking the carbonyl group of one amino acid with the amino group of the following amino acid. Several proteases are also capable of cleaving esters of amino acids, releasing the hydroxy moiety as one product and the acid group as a second product.

The specificity of many proteases is defined by the amino acid or amino acids on the amino terminal side of the site of cleavage of the peptide chain. If the amino acids on the amino side of the cleavage site is numbered as aa-1, aa-2, aa-3, etc. as they become farther removed from the cleavage site and aa+1, aa+2, aa+3 as they are found towards the carboxy terminal site of the cleavage site, any cleavage site can be defined by the amino acids present in these locations. Schematically, the identification process can be presented as shown below:

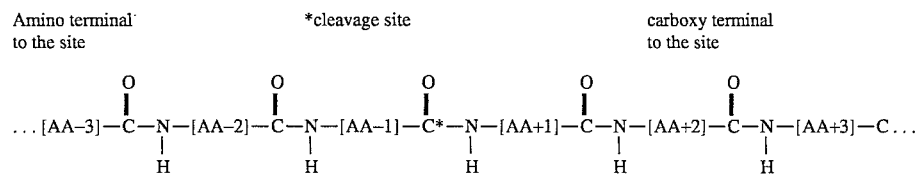

Using this system, the specificity of proteases can be defined by the range of sites that can be hydrolyzed by the enzyme. For example, trypsin will cleave a site when the aa-1 amino acid is Lys or Arg but only if the aa+1 amino acid is not a Pro residue. Factor X is a much more specific protease and requires the sequence Arg—[AA+1]. Although a number of amino acids can occupy the [AA +1] position and allow cleavage by the enzyme, Ile and Thr are preferred and the enzyme works slowly or not at all if the aa+1 amino acid is a Pro residue.

Substrate

A wide variety of peptide molecules which can be modified to allow their easy quantitation by a variety of means can be used as substrates for kinases, phosphatases and proteases. Preferred enzyme substrates are those which will be modified by only a single kinase, phosphatase or protease and have between 4–30 amino acid residues.

The peptide substrates of the present invention are molecules having the following characteristics: (1) a substrate for one or more protein kinase, phosphatase or protease; (2) a substrate labelled with a detector segment which allows the presence of the peptide to be measured, i.e., a substrate modified peptide; and (3) a substrate which can be separated from the product of the reaction by a variety of procedures including electrophoresis, chromatography, and extraction as well as others.

Substrates for Kinases—Several endogenous and exogenous substrates have been described for different protein kinases. In vitro, a single kinase can be shown to have over a dozen substrates (House et al., 1987). The mechanism by which a kinase can effectively distinguish between substrates in vivo is thought to involve compartmentalization and further regulatory mechanisms. Although activation of kinases often leads to profound physiological effects, the actual direct effect of substrate phosphorylation is only beginning to be understood.

Several common types of proteins, such as histones and caseins, have been shown to be good substrates for several protein kinases. This generality, though, often limits the effectiveness of kinase detection using such substrates by promoting a high background of phosphorylation by interfering kinases.

Studies on kinase substrates have led to the determination of the amino acid sequences necessary on a substrate for phosphorylation. This has allowed the synthesis of peptide substrates that are highly specific for individual kinase.

One of the best known artificial substrates is the heptapeptide Kemptide (Bramson et al., 1980), with the sequence:

L-R-R-A-S-L-G.

It is phosphorylated exclusively by the cAMP dependent protein kinase. Other specific substrates have been developed for other kinases, including cGMP-dependent protein kinase, calmodulin-dependent protein kinase (Pearson et al., 1985), and several Tyr kinases (Bowen et al., 1990).

Substrates for Phosphatases—Substrates for protein phosphatases can be derived from the products of the reactions of various protein kinases (reference made to prior section) with the substrate peptides.

Substrates for Proteases—If specific substrates are designed for monitoring the activity of particular proteases, the specificity of the protease must be kept in mind. For example, substrates for trypsin are made with an Arg or Lys residue as the aa-1 so that the enzyme will recognize the substrate. Trypsin can also cleave esters of Lys or Arg, and if an ester of p-nitro phenol is made to Lys or Arg, the enzyme can release p-nitro phenol as a product of hydrolysis.

The activity of the enzyme can then be measured by monitoring the amount of this product that has been produced, as the material absorbs light around 420 nm when present as a free hydroxy group but absorbs much less light as an ester.

However, some proteases will not cleave such esters—preventing their assay by such methods. In addition, other proteases cleave within their recognition site and will not release a colored ester the same way that trypsin will; for the cleavage occurs between two existing amino acids and not beyond the end of the peptide which defines a substrate. Thus, while easy to perform, these types of assays cannot be used with all proteases.

Preferred substrates for the protease Factor X have a Gly residue at the [AA–2] position. A well-known sequence, which is cleaved by this enzyme, is represented by the following formula:

Ile-Glu-Gly-Arg * (Ile or Thr)

where the * indicates the site of cleavage (Owen et al., 1974). Other proteases such as the HIV proteases have been less well studied, but peptide substrates for these proteases have been identified—sometimes through analysis of the cleavage sites of the enzyme within natural substrates. For example, the HIV protease has been shown to cleave the following peptides:

R-S-L-N-Y*P-Q-S-K-W

A-T-L-N-F*P-I-S-P-W where the * indicates the site of cleavage of the peptide by the protease.

Detector Segment

The substrate is labeled with a detector segment in a manner known to the art. The detector segment allows the amount of the peptide to be measured. The peptide detector segment, also referred to herein as a detection sequence, chemical tag or modification tag, is a chemical segment which allows the presence of the peptide to be detected by virtue of the ability of the chemical segment to absorb electromagnetic radiation such as visible light, or by virtue of its ability to fluoresce, i.e., emit light of a different wavelength than it absorbs, or both.

The peptide detector segment which is present on the peptide, now referred to as "substrate modified peptide," can be of several types commercially available and commonly known to those skilled in the art. Examples include dansyl, sulforhodamine, fluorescein, rhodamine B (Lissamine Rhodamine) or other tags which allow the measurement of the peptide to be performed.

Specialized Peptide Substrates

A number of specialized peptide substrates have been developed, each of which is tagged by a detector element as described above. Reference is made to Table 1 as follows for a listing of preferred proprietary peptide substrates:

be performed by separation of the modified and unmodified peptide species using electrophoresis and quantitation of the amount of either the residual substrate of the reaction, the product of the reaction, or both. The activity of protein kinases and phosphatases can be measured because of their ability to modify the specific peptide substrates described above by addition or removal of modified or unmodified phosphate groups from the peptide substrates of the invention.

The enzyme is incubated under conditions known to the art with the substrate modified peptide to form product modified peptides under conditions where the enzyme is active. Each of the enzymes is usually assayed at its optimum pH and temperature.

The enzyme may be incubated in a pure protein sample, a complex protein sample or a crude sample, all of which are defined above.

The detection of the activity of the enzyme is performed by separation of the modified and unmodified forms of the peptide in either qualitative or quantitative measurement of the amount of both species present in the sample.

Separation of the Substrate Modified Peptide From the Product Modified Peptide

The product modified peptide and substrate modified peptide can be separated from the product of the reaction by

TABLE 1

| Peptide | SEQ ID NO: | Sequence | Modification (detection tag) |
| --- | --- | --- | --- |
| Promega Peptide 1 | 1 | *-L-R-R-A-S-L-G | Dansyl |
| Promega Peptide 2 | 2 | *-L-R-R-A-S-V-A | Dansyl |
| Promega Peptide 3 | 3 | *-L-R-R-A-S-V-A | Sulforhodamine 101 |
| Promega Peptide 4 | 4 | *-R-F-A-R-K-G-S-L-R-Q-K-N-V | Lissamine Rhodamine# |
| Promega Peptide 5 | 5 | *-Q-R-R-Q-R-K-S-R-R-T-I | Lissamine Rhodamine |
| Promega Peptide 6 | 6 | *-P-L-S-R-T-L-S-V-A-A-K-K | Lissamine Rhodamine |
| Promega Peptide 7 | 7 | *-L-R-R-A-S-L-G | Lissamine Rhodamine |
| Promega Peptide 8 | 8 | *-D-R-V-Y-I-H-P-F | Lissamine Rhodamine |
| Promega Peptide 9 | 9 | *-R-S-L-N-Y-P-Q-S-U-W | Lissamine Rhodamine |
| Promega Peptide 10 | 10 | *-A-T-L-N-F-P-I-S-P-W | Lissamine Rhodamine |
| Promega Peptide 11 | 11 | *-P-L-S-R-T-L-S-V-A-A-K | Lissamine Rhodamine |

*Location of Detection Tag
Rhodamine B

A description of the formation, purification and representative uses of Promega Peptides 1–11 (SEQ ID NOS:1–11) follow in the examples.

Referring to Table 2, it has been determined that the following Promega Peptide substrates have specific utility for the named enzyme assay:

TABLE 2

| Enzyme | Promega Peptide Substrates |
| --- | --- |
| Kinases (in general) | Promega Peptides 1–8, 11* |
| Tyrosine Kinase | Promega Peptide 8 |
| Protein Kinase C | Promega Peptides 4, 5, 6, 11 |
| Protease | Promega Peptide 1–11 |
| HIV Protease | Promega Peptide 9–10 |
| Phosphatase | Modified (Phosphorylated) Promega Peptides 1–8, 11 |

*Refer to Table 1 for SEQ ID NO: listings

Measurement of Activity

Activity of an enzyme is determined by measuring the amount of product produced, i.e., the product modified peptide, or the amount of substrate unmodified by the action of the enzyme per unit of time, i.e., the substrate modified peptide. The measurement of the activity of the enzymes can a number of methods known to the art, such as electrophoresis, chromatography and extraction.

As used herein, chromatography includes the separation of materials by the movement of a solvent over a separation matrix. Such chromatography can be performed upon a silica gel matrix, a paper matrix, a derivatized material used for ionic, hydrophobic, or size exclusion separation of materials such as DEAE sephadex, Phenyl Sepharose, G25 Sephadex as well as other matrices well known to the art. Solvents for the separation will include aqueous, organic, non-organic, and mixtures of aqueous and organic and non-organic solvents.

Electrophoresis is the preferred procedure for separating the different peptide species present in a sample. Electrophoresis is a prior art technique that has a novel application in the present invention. In the prior art, it is used to effect separation of molecules for purification or analysis. The technique is of particular value in biochemistry because it is highly sensitive and it does not affect the structure of the biomolecules upon which it operates. The most common type of electrophoresis is zone electrophoresis.

In zone electrophoresis, the sample of interest is applied to one part of a solid support, and an electric field is established across the support. Under the motive force of the electric field, the sample molecules move through the support toward either the positive or negative electrode, depending on the net charge of the molecule. The extent to which the molecules move through a given support under a given electric field is referred to as the molecules' mobility, and generally depends upon the net charge, shape and size of the molecule. More specifically, the mobility of a molecule is directly proportional to the net charge of the molecule, and inversely proportional to the size and shape. Molecules with larger net charges have a greater mobility in a given electric field, due to a larger motive force. Larger and/or bulkier molecules, such as nucleic acids and proteins, have a greater frictional resistance to movement through the support, and hence, have less mobility. In contrast, smaller molecules, such as amino acids and enzymes have less frictional resistance and therefore demonstrate a greater mobility. The mobility of such smaller molecules is generally controlled by the size of these molecules rather than their shape.

The support media operates primarily as a means to minimize external disturbances, such as convection and diffusion, from influencing the mobility of the sample. The support media may also serve as a molecular filter or a pH stabilizing media. Typical support media for electrophoresis include paper, cellulose acetate, and gels of starch, polyacrylamide, and agarose. Paper and cellulose acetate media are most effective for separating compounds of low to medium molecular weight ($\leq 10,000$), such as amino acids or small peptides. The gels are more effective for separating high molecular weight compounds, such as nucleic acids and proteins. Starch gels have been used for separation of hemoglobin and plasma proteins, but the lack of reproducibility of the gel composition and pore size has limited their widespread use. Polyacrylamide gels may be consistently produced with specific pore sizes, and hence, may be used to selectively restrict the movement of certain larger molecules.

Agarose gel support media are typically useful for separation of very large molecules such as DNA, lipoproteins, immunoglobulins and enzyme complexes. Agarose is the neutral-charged polysaccharide fraction of agar, and an agarose gel is formed by suspending dry agarose in an aqueous buffer, heating until completely dissolved and then cooling the solution to room temperature. The pore size of the agarose gel is determined by and is inversely related to the initial concentration of agarose. Agarose gels also afford a simple method for the recovery of separated sample fractions, such as a particular DNA fragment. The gel portion which contains the fraction of interest is heated to liquify the gel, which is then physically separated from the sample fraction. In the present invention, however, agarose gel electrophoresis is used to separate peptides as small as 20 amino acids modified by the action of an enzyme.

Buffers are required and can be of many different types, depending upon the particular materials to be separated. However, the use of buffers in the pH range from 7.0 to 9.0 are common and are made using standard components such as phosphate or Tris. Most advantageously, the separations are performed in the horizontal mode using an agarose gel to hold the samples and employing Tris buffers in the pH range from 7.0 to 9.0.

The amount of the specific product modified peptide that has been modified by the enzyme under assay is then measured. The activity of the enzyme is detected by measurement of the modified and unmodified forms of the peptide. The measurement may be either qualitative or quantitative as defined below.

Quantitative Measurement

Spectroscopy

Quantitation can be performed using a spectrometer if the particular peptide used has been designed to allow its measurement by absorption of electromagnetic radiation, such as visible or ultraviolet light.

Fluorescence

Quantitation can also be performed by the use of a fluorometer, if the particular peptide used as a substrate can emit light of a particular wavelength after absorbing light of a different wavelength.

Chemiluminescence

Additionally, other types of quantitation, such as measurement of the production of light from a particular peptide substrate modified to produce light by chemiluminescence, can be performed.

The present invention is also directed to kits that utilize the process of the present invention. A basic kit for quantitating the presence or activity of an enzyme includes a container containing a bioreagent, which is a substrate modified peptide having specific reactivity to the enzyme, modified by chemical reaction to allow easy visualization/quantitation, and instructions for use.

The substrate modified peptide in the kit is preferably one of following peptides, depending upon the type of enzyme to be assayed as explained above: Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 9 (SEQ ID NO:9), Promega Peptide 10 (SEQ ID NO:10), and Promega Peptide 11 (SEQ ID NO:11). Reference is made to Table 2 above for substrate modified peptides specific for certain enzyme assays.

The kit could further include a container containing at least one buffer, which is compatible with the enzyme. The kit can also include a container containing at least one separation material for isolation of either a product modified peptide or the substrate modified peptide.

The present invention is also directed to a kit for quantitating the activity of the enzyme protease in a peptide substrate. The basic kit includes at least one container containing at least one substrate respectively for protease digestion, and instructions for use.

The amounts of the various reagents in the kits can be varied depending on a number of factors, such as the optimum sensitivity of the assay. The instructions for use are suitable to enable an analyst to carry out the desired assay. It is within the scope of this invention to provide manual test kits or test kits for use in automated analyzers.

The following examples are presented to illustrate the advantages of the present invention and to assist one of ordinary skill in making and using the same. The examples are not intended in any way to otherwise limit the scope of the disclosure or protection granted by the patent.

While precise descriptions are given for assay of protein kinases, phosphatases, and proteases in the following examples, it should be clear to one well versed in the art that the results of the present invention can be applied to the assay of a wide variety of enzymes including but not limited to: esterases, deesterases, amidases, deamidases, glycosidases, deglycosidases, ribosylases, deribosylases, methylases and demethylases either directly or with minor modifications such as would be expected to one familiar with the assay of such enzymes.

While the material presented below takes advantage of peptides which are chemically synthesized in vitro and some of which are commercially available, it should be noted that the invention can be performed by isolation of a peptide from a natural source by digestion of a larger precursor protein or peptide and isolation of the proper resulting fragment by methods well known in the art followed by its attachment to a detector segment as defined earlier.

EXAMPLES

Example 1

Synthesis of Promega Peptide 1 (SEQ ID NO:1) (Dansyl Kemptide) and Promega Peptide 2 (SEQ ID NO:2) ($V^6A^5$ Dansyl Kemptide)

A solution of Kemptide (Sigma Chemical Co., St. Louis, Mo.) and $V^6A^5$ Kemptide (Sigma Chemical Co., St. Louis, Mo.) was made by dissolving 5 milligrams (mg) of the peptide in I milliliter (ml) of 200 millimolar (mM) sodium borate buffer, pH 9.0. The solutions were placed into individual 1.5 ml Eppindorf tubes. A control solution of the buffer without peptide was also prepared by placing 1 ml of the buffer in a separate 1.5 ml Eppindorf tube. To each of these solutions was added 50 microliters (µl) of acetone containing 100 mg/ml dansyl chloride (Aldrich Chemical Co., Milwaukee, Wis.). After 5 minutes of incubation at room temperature, a small amount of precipitate was seen in the tubes.

A small amount of the material from the synthesis, approximately 0.5 µl, was applied to a silica gel ascending thin layer chromatography plate, and the plate was developed with a solution of methanol: chloroform: acetic acid having the following ratio: 50:20:1.

After the solvent had moved 12 centimeters (cm) up the plate, the plate was photographed under long-wave ultraviolet (UV) light on a transilluminator using Polaroid type 667 film and an orange filter (Tiffen Co.). The reactions containing the peptide each contained a new fluorescent product with a mobility slower than the species seen in the control reactions.

The unique product present in the Kemptide peptide reaction had a slightly slower mobility than that seen in the $V^6V^5$ Kemptide reaction. These unique peptides are the dansyl derivatives desired from these peptides and were renamed Promega Peptide 1 (SEQ ID NO:1) and Promega Peptide 2 (SEQ ID NO:2) for the Kemptide and $V^6A^5$ Kemptide derivative, respectively.

Example 2

Purification of Promega Peptides 1 (SEQ ID NO:1) and 2 (SEQ ID NO:2)

A column (2.5×15 cm) of Sephadex G25 fine (Sigma Chemical Co., St. Louis, Mo.) was made according to the recommendations of the manufacturer and equilibrated using 10% ethanol in 20 mM Tris pH 8.0. One ml of the synthesis solutions for the modified peptides Promega Peptide 1 (SEQ ID NO:1) or 2 (SEQ ID NO:2) was applied to the column and the column was then eluted using 10% ethanol, 20 mM Tris pH 8.0. Five ml fractions were collected and 2 µls of the fractions were analyzed by thin layer chromatography and photographed as described in Example 1.

Fractions 8–12 collected from the column were shown to contain the fluorescent modified peptide species, but did not contain significant levels of the unbound, spent derivitization reagent. These fractions were pooled and lyophilized to dryness to obtain purified, modified peptide pools of Promega Peptides 1 (SEQ ID NO:1) and 2 (SEQ ID NO:2).

Example 3

Assay of Protein Kinase Using Promega Peptides 1 (SEQ ID NO:') and 2 (SEQ ID NO:2)

Radioactive kinase assays were carried out as described in Walton et al., as modified and described here. Five µl Promega Peptide 1 (SEQ ID NO:1) were added to a reaction mixture containing 20mM Tris HCl (pH 7.4), 10 mM $MgCl_2$, 4 micrograms (µg) of cAMP-dependent protein kinase (both catalytic and regulatory subunits), in the presence or absence of 2 micromolar (µM) cAMP, in a volume of 50 µl.

The reaction began with the addition of 10 µl of solution containing 0.15 mM [$\gamma_{32}P$] ATP (about 0.05 Ci/mmol) and 10 mM $MgCl_2$. After a two minute incubation, the reaction was terminated by the addition of 30 µl of $H_3PO_4$ to a final concentration of 0.5%. To measure incorporation of radio-labelled phosphate into the peptide substrate, half the reaction mixture was spotted onto a Whatmann P81 filter. The filters were washed four times in a solution containing 0.5% $H_3PO_4$. Each wash lasted at least five minutes. After washing, the radioactivity present on the filters was measured in a scintillation counter. Both of the peptides showed increased phosphorylation in the presence of cAMP, indicating that they are substrates for cAMP-dependent protein kinase. The counts per minute (CPMs) resulting from the assays are given in Table 1 below:

TABLE 3

| Substrate | CPM (no cAMP) | CPM (+cAMP) | Stimulation |
|---|---|---|---|
| Kemptide | 5760 | 471,840 | 82 |
| Dansyl Kemptide | 3166 | 393,062 | 124 |
| Dansyl $V^6A^5$-Kemptide | 21044 | 581,682 | 28 |

Example 4

Separation of Phosphorylated Promega Peptides 1 (SEQ ID NO:1) and 2 (SEQ ID NO:2) from the Unphosphorylated Peptides by Thin Layer Chromatography Promega Peptides 1 (SEQ ID NO:1) and 2 (SEQ ID NO:2) were phosphorylated as described in Example 3 using non-radioactive ATP in a final volume of 60 µl. Samples from these reactions were spotted onto Whatman Silica Gel 60 A thin-layer chromatography plates (Sigma Chemical Co., St. Louis, Mo.), and the spots were developed with a solution containing 55% methanol, 40% chloroform, and 5% acetic acid. Once the solvent front neared the top of the plates, the plates were dried and examined under a UV light.

Referring now to FIG. 1, the non-phosphorylated species show the highest mobility, with an $R_f$ of 0.81; the phosphorylated peptides showed a lower mobility with an $R_f$ of 0.12.

Referring to FIG. 1, which is a photograph of a thin-layer chromatography (TLC) plate, the phosphorylated and non-phosphorylated Promega Peptides 1 (SEQ ID NO:1) and 2 (SEQ ID NO:2) have been spotted.

Lane 1: contains 2λ of non-phosphorylated Promega Peptide 1 (SEQ ID NO:1).

Lane 2: contains 5λ of phosphorylated Promega Peptide 1 (SEQ ID NO:1).

Lane 3: contains 2λ of non-phosphorylated and 5λ of phosphorylated Promega Peptide 1 (SEQ ID NO:1).

Lane 4: contains 2λ of non-phosphorylated Promega Peptide 2 (SEQ ID NO:2).

Lane 5: contains 5λ of phosphorylated Promega Peptide 2 (SEQ ID NO:2).

Lane 6: contains 2λ of non-phosphorylated and 5λ of phosphorylated Promega Peptide 2 (SEQ ID NO:2).

Example 5

Separation of Phosphorylated Promega Peptides I (SEQ ID NO:1) and 2 (SEQ ID NO:2) from the Unphosphorylated Peptides by Electrophoresis Promega Peptides 1 (SEQ ID NO:1) and 2 (SEQ ID NO:2) were phosphorylated as described in Example 3 with the following modifications:
1) no radioactivity was used;
2) incubation time was 1 hour; and
3) the reactions were stopped by quick freezing of the reaction by placing the tube containing the reaction in a dry ice/ethanol bath.

Glycerol was added to a final concentration of 5%, and 10 μl of each of the reactions (approximately 4 μl of peptide) were loaded onto a 0.8% agarose submarine gel, equilibrated with 50 mM Tris HCl, pH 8.0. The gel was run for one hour at 50 volts (V). Complete separation of the two species was observable fifteen minutes after starting the gel. After completion, the gel was viewed by a fluorometer to illuminate the dansylated peptides.

Figure 2:
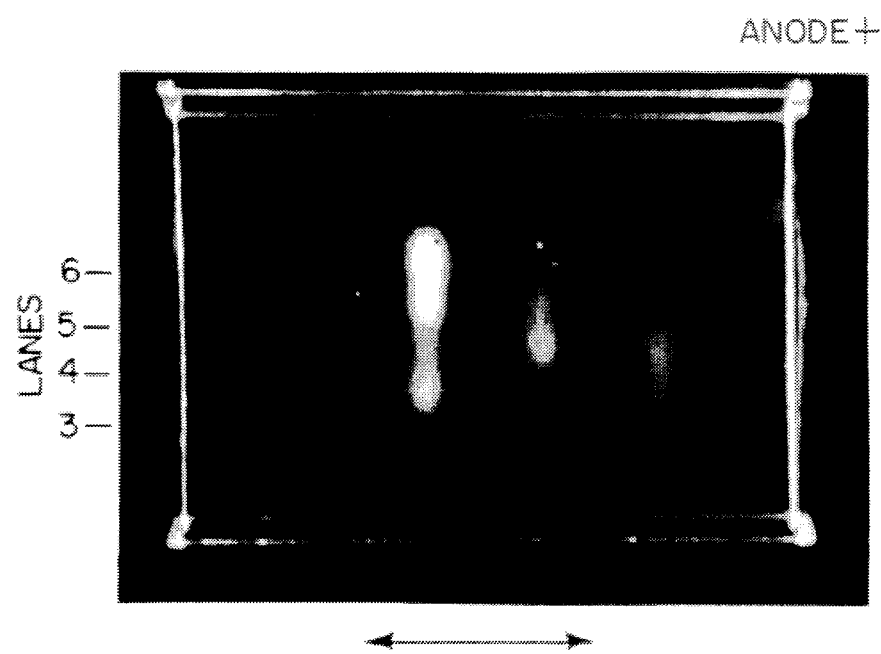
FIG. 2 is a photograph illustrating the separation of phosphorylated Promega Peptides 1 (SEQ ID NO:1) and 2 (SEQ ID NO:2) from the unphosphorylated peptides by electrophoresis in Example 5.

Reference is made to FIG. 2, which is a photograph of 0.8% agarose gel used to separate phosphorylated and non-phosphorylated Promega Peptides 1 (SEQ ID NO:1) and 2 (SEQ ID NO:2). The anode end of the gel is to the right:

Lane 3: contains non-phosphorylated Promega Peptide 1 (SEQ ID NO:1).

Lane 4: contains Promega Peptide 1 (SEQ ID NO:1) that has been partially phosphorylated.

Lane 5: contains partially phosphorylated Promega Peptide 2 (SEQ ID NO:2).

Lane 6: contains non-phosphorylated Promega Peptide 2 (SEQ ID NO:2).

The non-phosphorylated peptides 1 (SEQ ID NO:1) and 2 (SEQ ID NO:2), which have a net change of +1, migrated to the left of the origin. The phosphorylated peptide, which has a net change of −1, migrated to the right. Bands on the far right side are due to dansyl dye that did not react with the peptide during synthesis.

Example 6

Detection of Small Amounts of Protein Kinase Using Promega Peptide 1 (SEQ ID NO:1)

Promega Peptide 1 was phosphorylated under non-radioactive conditions as described in Example 3 with varying amounts of cAMP-dependent protein kinase for 15 minutes. The reactions were stopped by heating the reaction samples at 95° C. for 10 minutes. Glycerol was added to a final concentration of 1%, and 20 μl of each reaction mixture were loaded onto a 0.8% agarose submarine gel. The gel was run for 1 hour at 75 V, and dansylated peptide was detected by UV light.

The phosphorylated peptide could be detected in the reaction mixture that had been incubated with 5 nanograms (ng) of cAMP-dependent protein kinase, and intensity of the phosphorylated band increased with the amount of kinase that had been present in the reaction mixture.

Figure 3:
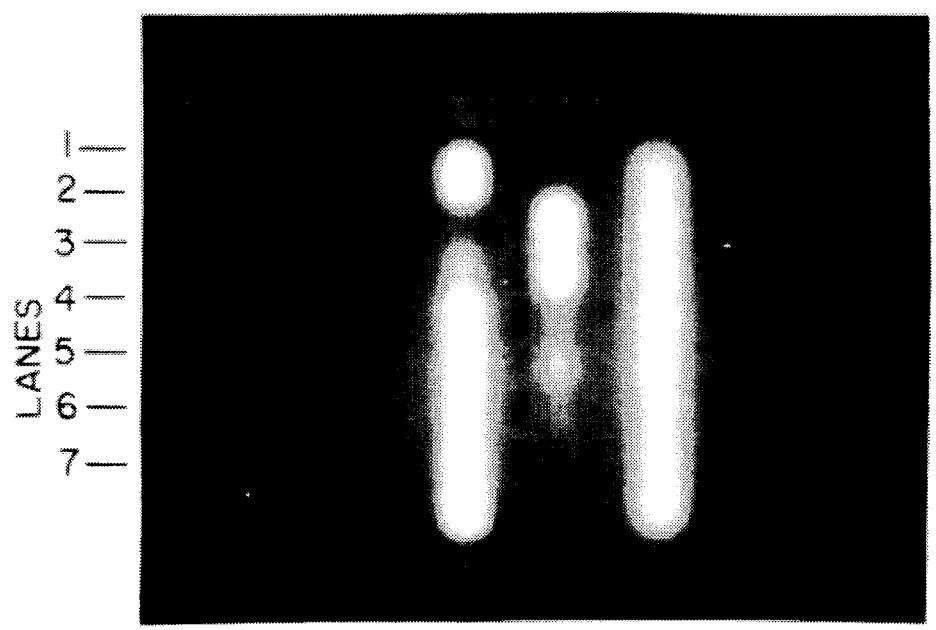
FIG. 3 is a photograph illustrating the detection of small amounts of protein kinase using Promega Peptide 1 (SEQ ID NO:1) in Example 6.

Reference is made to FIG. 3, which is a photograph of a 0.8% agarose gel used to determine the detection limit of cAMP-dependent protein kinase (CAPK) using Promega Peptide 1 (SEQ ID NO:1):

Lane 1: contains 2.5 μg Promega Peptide 1 (SEQ ID NO:1) and no cAMP-dependent kinase.

Lane 2: contains 2.5 μg Promega Peptide 1 (SEQ ID NO:1) and 225 ng CAPK.

Lane 3: contains 2.5 μg Promega Peptide 1 (SEQ ID NO:1) and 45 ng CAPK.

Lane 4: contains 2.5 μg Promega Peptide 1 (SEQ ID NO:1) and 20 ng CAPK.

Lane 5: contains 2.5 μg Promega Peptide 1 (SEQ ID NO:1) and 5 ng CAPK.

Lane 6: contains 2.5 μg Promega Peptide 1 (SEQ ID NO: 1) and 2.5 ng CAPK.

Lane 7: contains 2.5 μg Promega Peptide 1 (SEQ ID NO:1) and 0.25 ng CAPK.

The non-phosphorylated Promega Peptide 7 (SEQ ID NO:7) migrated to the left of the origin. The phosphorylated Promega Peptide 7 (SEQ ID NO:7) migrated to the right of the origin. Bands on the far right are due to free dye that did not react with the peptide during synthesis.

Example 7

Detection of Protein Kinase Activity in Crude Extracts using Promega Peptide 1 (SEQ ID NO:1)

Crude extracts were prepared from rat brain as described in Example 14 (infra.) without applying the sample to the DEAE column. Ten μl of diluted homogenate were incubated with protein kinase C reaction buffer. (described in Example 13, infra.), 10 μl Promega Peptide 1 (SEQ ID NO:1), and 2 μM cAMP in a final volume of 100 μl for a time ranging between 0 seconds to 10 minutes.

Reactions were stopped by heating to 95° C. for 10 minutes. Glycerol was added to 4%, and 10 μl of the solutions were applied to an 8% agarose gel as described in Example 6 (supra.). Visualization of phosphorylated peptide was achieved by viewing the gel under UV light and could be seen within 10 minutes.

The cAMP-dependent protein kinase was detectable at all incubation times.

Figure 4:
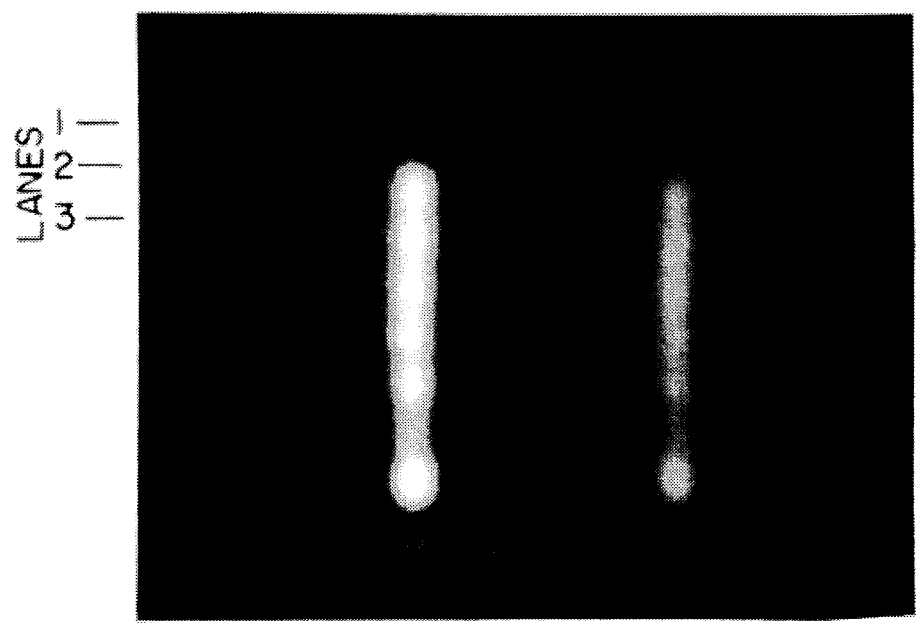
FIG. 4 is a photograph illustrating the detection of protein kinase activity in crude extracts using Promega Peptide 1 (SEQ ID NO:1) in Example 7.

Reference is made to FIG. 4, which is a photograph of a 0.8% agarose gel showing the separation of non-phosphorylated Promega Peptide 1 (SEQ ID NO:1) from Promega Peptide 1 (SEQ ID NO:1) phosphorylated by cAMP-dependent protein kinase present in homogenated rat brain as described in Example 7. The positively-charged anode end of the gel is on the left.

Lane 3 shows Promega Peptide incubated with homogenate for 15 seconds. Phosphorylated peptide migrates to the left, non-phosphorylated peptide to the right. The other lanes are not relevant to the experiment.

Example 8

Synthesis of Promega Peptide 3 (SEQ ID NO:3) (Sulforhodamine 101 Derivative of $V^6A^5$ Kemptide)

The peptide $V^6A^5$ Kemptide was dissolved in 200 mM sodium borate buffer, pH 9.0, and 200 μl of this solution was placed in a 1.5 ml Eppindorf tube. To this tube was added 500 μl of acetonitrile containing 10 mg sulforhodamine 101 acid chloride (Aldrich Chem. Co., Milwaukee, Wis.). The reaction mixture was allowed to incubate for 10 minutes at room temperature, and 300 μl of water was added to the tube.

An agarose gel (1% w/w agarose in 20 mM Tris hydrochloride, pH 8.0) was prepared by suspending the agarose in the buffer and heating to boiling in a microwave. The solution was mixed by stirring, and the molten agarose was poured into a BioRad horizontal gel apparatus (Biorad Co., Richmond Calif., Cat. No. 170-4307) containing a comb to provide sample slots.

After the solution had solidified by cooling to room temperature, the comb was removed from the gel and a gel approximately 0.5 cm thick was produced. Twenty microliters of the reaction mixture described above was added to 5 μl of 80% glycerol, and the mixture was added to one of the loading wells in the gel. The gel was placed in the running apparatus of the manufacturer and 20 mM Tris hydrochloride, pH 8.0 was added as a running buffer according to the instructions of the manufacturer. Electrophoresis was performed at 200 V for 40 minutes.

One colored species, which represents spent sulforhodamine 101 acid chloride, was seen migrating towards the positive electrode, while a second species which was composed of the modified peptide, was seen migrating with a slightly slower mobility towards the negative electrode. Thus this analysis confirmed that the Sulforhodamine 101 acid chloride derivative of $V_6A^5$ Kemptide had been synthesized. The peptide was renamed Promega Peptide 3 (SEQ ID NO:3).

Reference is made to FIG. 5, which is a photograph of the agarose gel used to confirm the synthesis of Promega Peptide 3 (SEQ ID NO:3) photographed under UV light showing the separation of the components present in modification reactions made during synthesis of Promega Peptide 3 (SEQ ID NO:3). The gel was photographed such that the end of the gel oriented towards the negative electrode is located at the top of the photograph and the lanes are numbered from left to right. The samples in the lanes are as follows:

Lanes 1 and 2: no sample;
Lane 3: 20 μl of the synthetic reaction listed in Example 8 describing the synthesis of Promega Peptide 3 (SEQ ID NO:3);
Lane 4: an equivalent sample of a mock reaction made as described in Example 8 but lacking the peptide substrate— this reaction allows the mobility of the spent fluorescent reagent to be measured and can be seen as the highly fluorescent species migrating towards the positive electrode;
Lane 5-end: not relevant to this discussion.

The fluorescent species present in Lane 2 which migrates towards the negative electrode is Promega Peptide 3 (SEQ ID NO:3) which has been synthesized in the reaction described in Example 8.

Example 9

Purification of Promega Peptide 3 (SEQ ID NO:3)

The solution of Promega Peptide 3 (SEQ ID NO:3) was applied to a 2.5×15 cm column of Sephadex G25 equilibrated with 50 mM ammonium bicarbonate pH 7.8. The column was eluted with 50 mM ammonium bicarbonate, and fractions of approximately 8 ml were collected. Twenty-five microliters of these fractions was added to 10 μl of 80% glycerol. Twenty microliters of these samples were applied to an agarose gel made as described in Example 8 and the gel was run as described in that example.

Those fractions which contained the modified peptide, as demonstrated by containing the colored species which migrated towards the negative electrode, were pooled and lyophilized to produce purified Promega Peptide 3 (SEQ ID NO:3). A solution of this material was made by dissolving the resulting material in 0.5 ml distilled water.

Reference is made to FIG. 6, which is a photograph of the agarose gel used to analyze the components present in samples of column fractions collected during purification of Promega Peptide 3 (SEQ ID NO:3) by fractionation of the reaction mixture on Sephadex G25. The gel was photographed under UV light as described in Example 1, and the gel is oriented such that the region of the gel oriented towards the negative electrode is towards the top of the photograph. The lanes are numbered from left to right. The lanes showing no fluorescent species will be ignored and not numbered:

Lane 1: a sample of fraction 5 (for details on the composition of the samples, see example 8);
Lane 2: a sample of fraction 6;
Lane 3: a sample of fraction 7;
Lane 4: a sample of fraction 8;
Lane 5: a sample of fraction 9;
Lanes 6-end: not pertinent to this discussion.

The samples in lanes 1–5 contained the fluorescent species which migrated towards the negative electrode that was identified in Example 8 as Promega Peptide 3 (SEQ ID NO:3). These fractions were further treated as described in Example 8.

Example 10

Assay of Protein Kinase Using Promega Peptide 3 (SEQ ID NO:3)

Fifteen microliters of Promega Peptide 3 (SEQ ID NO:3) were incubated with reaction buffer containing 20 mM HEPES (pH 7.4), 50 mM $MgCl_2$, 15 mM ATP, and 2 μg cAMP-dependent protein kinase for 2 hours at room temperature. The reaction was stopped by incubating the reaction mixtures for 10 minutes at 95° C. Glycerol was added to a final concentration of 4%, and 10 μl of the reaction were loaded on to an 8% agarose gel as described in Example 6.

Electrophoresis of the peptide showed that the phosphorylated species could be separated from the non-phosphorylated species. In addition, the separation could be seen visibly as well as fluorescently. The separation was based on the difference in the charges on the two species as described in Example 5. The separation was visible within ten minutes of the beginning of the electrophoresis.

Figure 7:
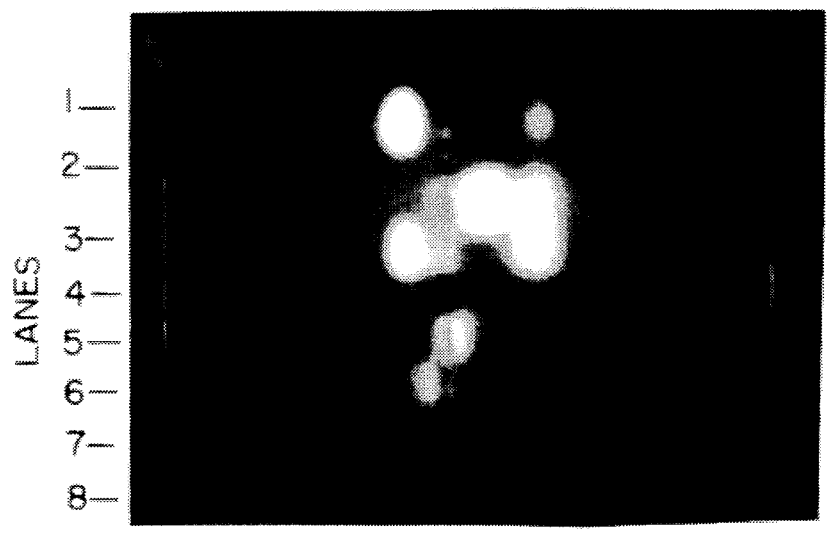
FIG. 7 is a photograph illustrating an assay of protein kinase using Promega Peptide 3 (SEQ ID NO:3) in Example 10.

Reference is made to FIG. 7, which is a photograph of an agarose gel showing the separation of phosphorylated and non-phosphorylated Promega Peptide 7 (SEQ ID NO:7). The anode end of the gel is on the right.

Lane 1: non-phosphorylated Promega Peptide 3 (SEQ ID NO:3);
Lane 2: Promega Peptide 3 (SEQ ID NO:3) that had been incubated with cAMP-dependent protein kinase for 30 minutes at room temperature (23° C.);
Lanes 3–8: not relevant to this example.

The positively charged non-phosphorylated peptide migrated to the left of the origin. The phosphorylated peptide migrated to the right.

Example 11

Synthesis of Promega Peptides 4 (SEQ ID NO:4), 5 (SEQ ID NO:5), 6 (SEQ ID NO:6)

The peptide listed [ser25] protein kinase C (Bachem Inc., Torrence, Calif., Cat. No. PPHA115) was dissolved in distilled water to a concentration of 10 mg/ml. Two 100 μl samples of this solution were placed in 1.5 ml Eppindorf tubes with 600 μl water and 100 μl 200 mM sodium borate, pH 9.0. This solution was mixed by vortex, and 200 μl of 10 mg/ml lissamine rhodamine sulfonyl chloride, (Molecular Probes, Eugene, Oreg.) in acetonitrile was added to the reaction. After 15 minutes of incubation at room temperature, an additional 100 μl borate buffer and 200 μl lissamine rhodamine in acetonitrile was added to one of the 1.5 ml Eppindorf tubes. The tubes were allowed to incubate for an additional 30 minutes at room temperature.

Five and 10 μl samples of the 2 reactions described above were applied to a 0.8% agarose gel made and equilibrated in 50 mM Tris-Cl buffer, pH 8.0. The gel was electrophoresed at 100 V for 1 hour, and photographed on a transilluminator as described above.

The reaction mixture which was given a single addition of lissamine rhodamine showed a unique band with a high mobility towards the negative electrode which was assigned the name Promega Peptide 4 (SEQ ID NO:4). The samples from the reaction given two lissamine additions did not show this peptide but apparently did contain unique colored species which moved towards the positive electrode. The nature of these species was not determined.

Figure 8:
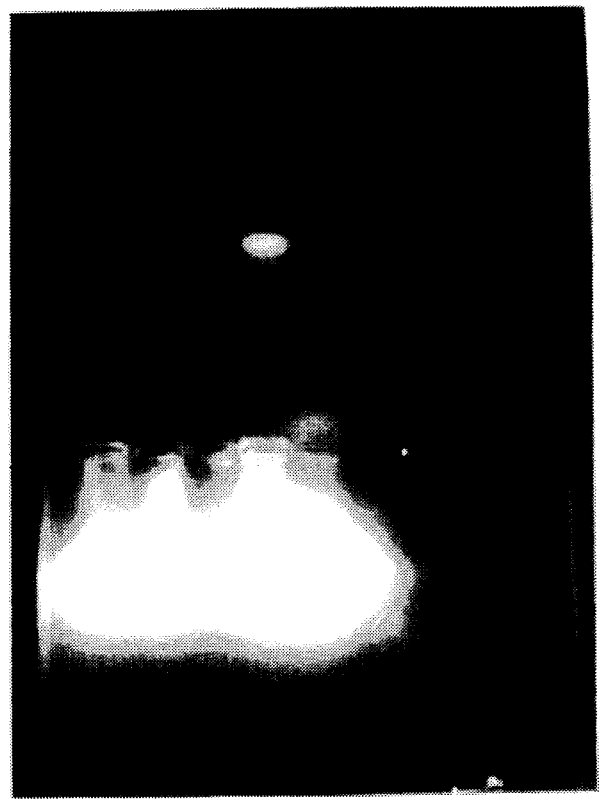
FIG. 8 is a photograph illustrating the synthesis of Promega Peptide 4 (SEQ ID NO:4) in Example 11.

Reference is made to FIG. 8, which is a photograph of the agarose gel used to analyze the components present in samples of the reaction mixes tested for production of Promega Peptide 4 (SEQ ID NO:4). The gel was photographed under UV light as described in Example 1 and the gel is oriented such that the region of the gel oriented towards the negative electrode is towards the top of the photograph. The lanes are numbered from left to right:

Lane 1: 5 μl reaction mix given a single lissamine rhodamine addition (see example 11 for a full description of the samples);

Lane 2: 5 μl reaction mix given a second lissamine rhodamine addition;

Lane 3: blank;

Lane 4: 10 μl reaction mix given a single reagent addition;

Lane 5: 10 μl reaction mix given a second reagent addition.

The fluorescent material seen having a mobility towards the negative electrode greater than that seen for the spent reagent (which migrates towards the positive electrode) in lanes 1 and 4 was identified as Promega Peptide 4 (SEQ ID NO:4).

The peptide H-9685, (Bachem Bioscience Inc., Philadelphia, Pa..) was dissolved in water to a concentration of 10 mg/ml. Fifty microliters of this material was mixed with 300 μl water and 50 μl 200 mM sodium borate buffer, pH 9.0. One hundred microliters of 10 mg/ml lissamine rhodamine sulfonyl chloride (Molecular Probes, Eugene, Oreg.), dissolved in acetonitrile, was added to the solution. The reaction was incubated at room temperature for 30 minutes. Four microliters of the material were applied to an agarose gel (0.8% w/v) in 10 mM Tris-Cl, pH 8.0. The gel was run as above using 10 mM Tris-Cl as a running buffer and photographed on a transilluminator as described above. The gel contained one species which rapidly migrated towards the negative electrode which was named Promega Peptide 5 (SEQ ID NO:5).

Figure 9:
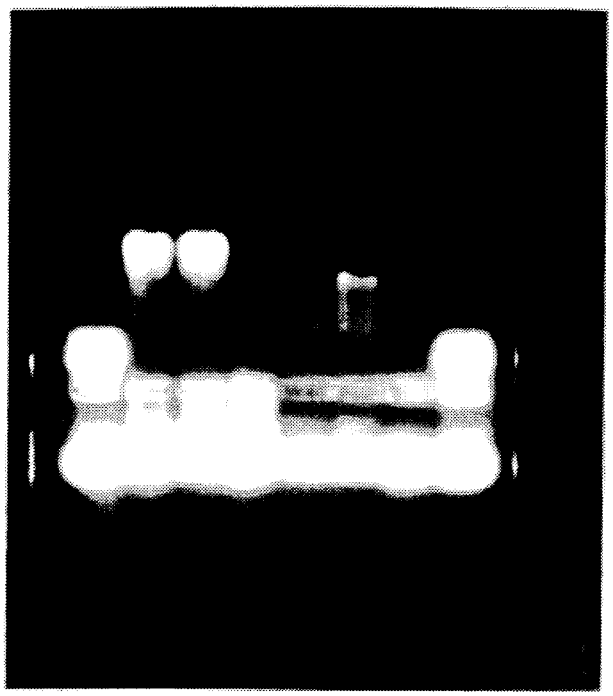
FIG. 9 is a photograph illustrating the synthesis of Promega Peptide 5 (SEQ ID NO:5) in Example 11.

Reference is made to FIG. 9, which is a photograph of the agarose gel used to analyze the components present in samples of the reaction mixes tested for production of Promega Peptide 5 (SEQ ID NO:5). The gel was photographed under UV light as described in Example 1 and the gel is oriented such that the region of the gel oriented towards the negative electrode is towards the top of the photograph. The lanes are numbered from left to right:

Lane 1: sample of the reaction mix involved in the synthesis of Promega Peptide 7 (SEQ ID NO:7) described in Example 20;

Lane 2: sample of the reaction mix involved in the synthesis of Promega Peptide 5 (SEQ ID NO:5);

Remaining lanes: not involved.

The fluorescent species migrating towards the negative electrode in Lane i with a mobility slower than that seen for the spent reagent migrating towards the positive electrode was identified as Promega Peptide 7 (SEQ ID NO:7); the fluorescent species migrating towards the negative electrode with a mobility faster than that seen for the spent reagent migrating towards the positive electrode in Lane 2 was identified as Promega Peptide 5 (SEQ ID NO:5).

Peptide PPHA117 was dissolved in water to a concentration of 10 mg/ml and duplicate 100 μl samples of this solution was placed in individual 1.5 ml Eppindorf tubes. To these tubes was added 600 μl water and 100 μl sodium borate buffer, pH 9.0. Two hundred microliters of acetonitrile containing 10 mg/ml of lissamine rhodamine sulfonyl chloride were added to each tube. The tubes were incubated for 15 minutes at room temperature. At this time, 20 μl I molar (M) NaOH were added to one of the tubes followed by an additional 200 μl lissamine rhodamine solution in acetonitrile. After an additional 5 minutes, 5 μl samples of the reaction solution was applied to an 0.8% agarose gel buffered with 50 mM Tris-Cl, pH 8.0. The gel was run as described above and photographed on a transilluminator.

Figure 10:
FIG. 10 is a photograph illustrating the synthesis of Promega Peptide 6 (SEQ ID NO:6) in Example 11.

Referring to FIG. 10, the photograph indicates that a rapidly moving fluorescent product was migrating towards the negative electrode. This component was named Promega Peptide 6 (SEQ ID NO:6). Shown in FIG. 10 is a photograph of the agarose gel used to analyze the components present in samples of the reaction mixes tested for production of Promega Peptide 6 (SEQ ID NO:6). The gel was photographed under UV light as described in Example 1 and the gel is oriented such that the region of the gel oriented towards the negative electrode is towards the top of the photograph. The lanes are numbered from left to right:

Lane 1: 5 μl of the reaction used for synthesis of Promega Peptide 6 (SEQ ID NO:6) not given sodium hydroxide treatment;

Lane 2: 5 μl reaction used for synthesis of Promega Peptide 6 (SEQ ID NO:6) given sodium hydroxide;

Lanes 3–4: not involved in this study;

Lane 5: same as Lane 1 but 10 μl of reaction;

Lane 6: same as Lane 2 but 10 μl of reaction.

The fluorescent species migrating towards the negative electrode in the lanes with a mobility slightly faster than that seen for the mobility of the spent reagent migrating towards the positive electrode was identified as Promega Peptide 6 (SEQ ID NO:6).

Example 12

Purification of Promega Peptides 4 (SEQ ID NO:4), 5 (SEQ ID NO:5), and 6 (SEQ ID NO:6)

In order to purify the peptides described in Example 11, a 2 ml bed volume of SP Trisacryl (Biotechnics, Inc.) was poured and equilibrated in 20 mM ammonium bicarbonate buffer, pH 7.8. The 2 reaction mixtures described for synthesis of Promega Peptide 4 (SEQ ID NO:4) were applied to the column. Six 5 ml washes of 20 mM ammonium bicarbonate buffer were applied to the column while 5 ml fractions were collected. These fractions eluted the bulk of the spent reagent as determined by analysis of samples of the fractions by agarose gel electrophoresis as described above.

Ten milliliters of 1M ammonium bicarbonate was then applied to the column and 1.5 ml fractions were collected. As the 1M buffer migrated through the column, a second colored species eluted which was shown to be the derived peptide by agarose gel electrophoresis. The fractions containing this derived peptide were lyophilized and resuspended in water to produce the stock pool of Promega Peptide 4 (SEQ ID NO:4).

The stock pools of Promega Peptides 5 (SEQ ID NO:5) and 6 (SEQ ID NO:6) were made as described above with the exception that Promega Peptide 6 (SEQ ID NO:6) was eluted from the Trisacryl SP column with 500 mM ammonium bicarbonate, pH 7.8.

Example 13

Detection of Protein Kinase C Activity Using Promega Peptides 4 (SEQ ID NO:4), 5 (SEQ ID NO:5), and 6 (SEQ ID NO:6)

Fifteen microliters of Promega Peptide 5 (SEQ ID NO:5) were incubated in protein kinase C reaction buffer (20 mM HEPES (pH 7.4), 1.3 mM $CaCl_2$, 1 mM DTT, 10 mM $MgCl_2$, 200 µg/mL phosphatidyl serine, 15 mM ATP), and 1 µg Protein Kinase C for 2 hours at room temperature in a final volume of 40 µl. The reaction was stopped by heating the reaction solution to 95° C. for ten minutes. Glycerol was added to a final concentration of 4%, and 10 µl solution were loaded on an 8% agarose gel as described in Example 5.

The separation of the phosphorylated and non-phosphorylated species was based on the difference in charges as described in Example 5, and could be seen under UV light within 20 minutes.

Figure 11:
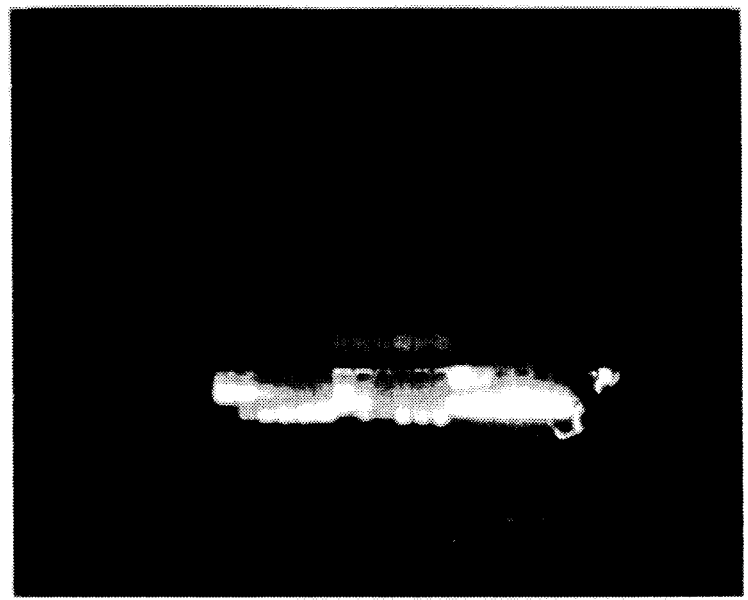
FIG. 11 is a photograph illustrating the detection of protein kinase C activity using Promega Peptides 4 (SEQ ID NO:4), 5 (SEQ ID NO:5), and 6 (SEQ ID NO:6) in Example 13.

Reference is made to FIG. 11, which is a photograph of a 0.8% agarose gel used to separate phosphorylated and non-phosphorylated Promega Peptides 4 (SEQ ID NO:4), 5 (SEQ ID NO:5), 6 (SEQ ID NO:6). The peptides were incubated with varying amounts of protein kinase C as described in Example 13. The positively charged anode end of the gel is toward the top:

Lanes 1–6: contain Promega Peptide 4 (SEQ ID NO:4).
Lanes 7–12: contain Promega Peptide 5 (SEQ ID NO:5).
Lanes 13–18: contain Promega Peptide 6 (SEQ ID NO:6).

The following data indicate the number of moles of protein kinase C present during each incubation.

Lanes 1, 7, 13: $730 \times 10^{-15}$ moles PKC (1 µg)
Lanes 2, 8, 14: $145 \times 10^{-15}$ moles PKC
Lanes 3, 9, 15: $14.5 \times 10^{-15}$ moles PKC
Lanes 4, 10, 16: $7.25 \times 10^{-15}$ moles PKC
Lanes 5, 11, 17: $1.45 \times 10^{-15}$ moles PKC
Lanes 6, 12, 18: $730 \times 10^{-18}$ moles PKC Example 14

Detection of Protein Kinase C Activity in Crude Samples Using Promega Peptide 6 (SEQ ID NO:6)

The brains from 100 adult male rats were obtained from Harlan Sprague Dawley (Indianapolis, Ind.). The brains were homogenized with a PolyTron (Model SDT 1810, Tekmar) in 250 ml buffer containing 20 mM Tris buffer (pH 7.5), 10 mM EGTA, 2 mM EDTA, 5 mM DTT, 1 mM PMSF, 10 mg/L Leupeptin, and 10 mg/L aprotinin. The homogenate was centrifuged for 20 minutes at 9000×g and filtered through glass wool. The liquid portion was then adjusted to pH 7.9, and diluted with water until the conductance was less than 0.8 mmho. The diluted solution was then applied to a 250 mL DEAE anion exchange column equilibrated in 20 mM Tris (pH 7.5), 2 mM EDTA, 2 mM EGTA, and 1 mM DTT. After loading, the column was washed with 1 liter (L) of buffer, and protein was eluted in a linear salt gradient ranging from 0.0M NaCl to 0.4M NaCl.

Column fractions were assayed for protein 20 kinase C activity by two methods: radioactively, which is known to the art and described by Walton et al., 1987, and non-radioactively as described below: 10 µl Promega Peptide 6 (SEQ ID NO:6) were incubated with protein kinase C reaction buffer (described in Example 13) for 30 minutes at room temperature in a final volume of 40µl. The reactions were stopped by heating the reaction mixtures to 95° C. for ten minutes. Glycerol was added to a final concentration of 4%, and 25 µl were applied to an 8% agarose gel, which was run as described in Example 5.

The phosphorylated peptide was visualized under UV light and could be distinguished from non-phosphorylated peptide within 15 minutes. Comparison of the results of the non-radioactive assay with the results of the radioactive assay showed that protein kinase C detected in fractions by 1 method was reliably detected by the other method.

Figure 12:
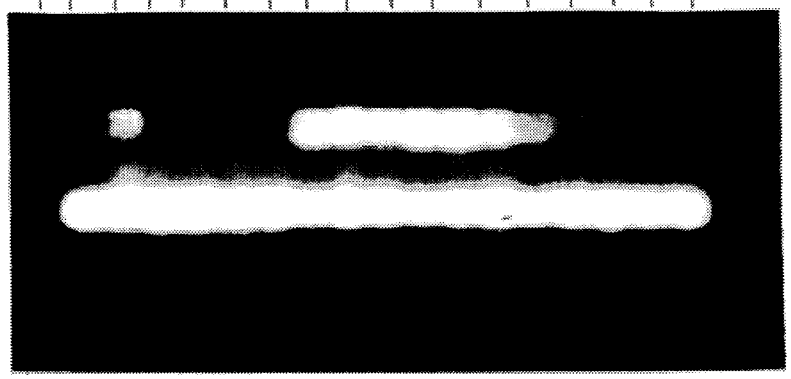
FIG. 12 is a photograph illustrating the detection of protein kinase C activity in crude samples using Promega Peptide 6 (SEQ ID NO:6) in Example 14.

Reference is made to FIG. 12, which is a photograph of a 0.8% gel used to detect the presence of protein kinase C in DEAE column fractions. Partial purification of the enzyme and reaction conditions are described in Example 14. The positively charged anode end of the gel is toward the top. The following data indicates the contents of the lanes of the gel.

| Lane | Contents | Lane | Contents |
| --- | --- | --- | --- |
| 1 | Blank | 10 | 39 |
| 2 | Homogenate | 11 | 42 |
| 3 | Blank | 12 | 45 |
| 4 | Blank | 13 | 48 |
| 5 | Fraction 10 | 14 | 51 |
| 6 | "F" 20 | 15 | 55 |
| 7 | F 30 | 16 | 60 |
| 8 | F 30 | 17 | 70 |
| 9 | F 36 | | |

The non-phosphorylated peptide migrated to the bottom of the gel. The phosphorylated peptide, which had a net charge of zero, remained at the origin.

Example 15

Detection of Small Amounts of Protein Kinase C Using Promega Peptides 4 (SEQ ID NO:4), 5 (SEQ ID NO:5) and 6 (SEQ ID NO:6)

Five microliters of Promega Peptide 5 (SEQ ID NO:5) and 6 (SEQ ID NO:6) or 2.5 µl of Promega Peptide 4 (SEQ ID NO:4) were incubated with a solution containing 18 µl protein kinase C reaction buffer (described in Example 13) and decreasing amounts of protein kinase C, containing between 60 ng and 60 picograms (pg), for 30 minutes at room temperature. Reactions were stopped by heating the reaction mixtures to 95° C. for 10 minutes. Glycerol was added to a final concentration of 4%, and 25 µl of the solution were applied to an 8% agarose gel as described in Example 5.

Referring to FIG. 11, the detection of phosphorylated peptide was observed under UV light, and detection limits noted. Six hundred picograms of protein kinase C could be detected by Promega Peptide 4 (SEQ ID NO:4), 3ng by Promega Protein 5 (SEQ ID NO:5), and 3 ng by Promega Protein 6 (SEQ ID NO:6).

Example 16

Assay of Pure Proteases Using Promega Peptides

The proteases Modified Trypsin [sequencing grade] (Promega Corp., Madison, Wis.) and Endoprotease Lys C [sequencing grade] were dissolved in A buffer (50 mM ammonium bicarbonate, pH 7.8). These stocks were diluted with A buffer to produce stocks containing 0.1, 0.01, and 0.0001 µg protease per 4 µl of liquid. Independent incubations of 4 µl of each of the different protease concentrations were performed with Promega Peptides 5 (SEQ ID NO:5), 6 (SEQ ID NO:6), 7 (SEQ ID NO:7) (5 μl of the stocks described above) in a 20 μl reaction mixture containing: 5 μl peptide; 4 μl protease; and 11 μl A buffer. Control reaction mixtures were made for each of the peptides which had an additional 4 μl of A buffer added in place of the protease.

After 90 minutes at 37° C., the samples were loaded into a 0.8% agarose gel made in 20 mM Tris, pH 8.0. The samples were electrophoresed at 150 V. When the control peptide sample had migrated about 0.5 inch from the loading well, the gels were photographed on a transilluminator as described above. The incubations made with trypsin displayed new peptide species as revealed by their mobility at all protease level and for all peptides as was expected if the protease could digest such peptides when labeled with the detection tag.

Figure 13:
FIG. 13 is a photograph of an agarose gel used to analyze peptide species produced in the digestion of Promega Peptide 6 (SEQ ID NO:6) by modified trypsin and Endoprotease Lys C in Example 16.

Reference is made to FIG. 13, which is a photograph of the agarose gel used to analyze the peptide species produced in the digestion of Promega Peptide 6 (SEQ ID NO:6) by modified trypsin and Endoprotease Lys C. The gel was photographed under UV light as described in Example 1 and the gel is oriented such that the end of the gel which was oriented towards the negative electrode is towards the top of the photograph. The lanes are numbered from left to right. Lane 1 identifies a control reaction sample which did not contain any added protease (see Example 16 for a more complete description of the samples if desired); Lane 2, a sample of the digestion of Promega Peptide 6 (SEQ ID NO:6) by 0.1 μg Endoprotease Lys C; Lane 3, a sample of the digestion of Promega Peptide 6 (SEQ ID NO:6) by 0.01 μg Endoprotease Lys C; Lane 4, a sample of the digestion of Promega Peptide 6 (SEQ ID NO:6) by 0.001 μg Endoprotease Lys C; Lane 5, a sample of the digestion of Promega Peptide 6 (SEQ ID NO:6) by 0.1 μg Modified Trypsin; Lane 6, a sample of the digestion of Promega Peptide 6 (SEQ ID NO:6) by 0.01 μg Modified Trypsin; and Lane 7, a sample of the digestion of Promega Peptide 6 (SEQ ID NO:6) by 0.001 μg Modified Trypsin. Note that fluorescent species with mobilities altered from that seen for Promega Peptide 6 (SEQ ID NO:6) are seen in the lanes containing samples from incubation of the peptide with moderate and high levels of added protease.

These results indicate that this method cannot only be used to assay proteases but a panel of peptides can be used to indicate the specificity of an unknown protease.

Figure 14:
FIG. 14 is a photograph of an agarose gel used to analyze peptide species produced in the digestion of Promega Peptide 5 (SEQ ID NO:5) and Promega Peptide 7 (SEQ ID NO:7) by modified trypsin and Endoprotease Lys C in Example 16.

Reference is made to FIG. 14, which is a photograph of the agarose gel used to analyze the peptide species produced in the digestion of Promega Peptides 5 (SEQ ID NO:5) and 7 (SEQ ID NO:7) by Modified Trypsin and Endoprotease Lys C. The gel was photographed under UV light as described in Example 1 and the gel is oriented such that the end of the gel which was oriented towards the negative electrode is towards the bottom of the photograph. The lanes are numbered from left to right. The first seven lanes containing fluorescent species contain Promega Peptide 5 (SEQ ID NO:5) samples and the second seven lanes containing fluorescent species contain the Promega Peptide 7 (SEQ ID NO:7) samples. The samples in the lanes comprising the first set of seven lanes containing fluorescent species are: Lane 1, control incubation without protease; Lanes 2, 3 and 4, incubations including 0.1, 0.01, and 0.001 μg Endoprotease Lys C, and 0.001 μg Modified Trypsin, respectively; Lanes 5, 6 and 7, incubations including 0.1, 0.01, and 0.001 μg Modified Trypsin, respectively. The samples in the second set of seven lanes containing fluorescent species are in the same relative order as described for the first set of seven lanes described above.

The samples incubated with Endoprotease Lys C did not display as large an amount of product peptide formed as did the trypsin incubated samples and the Promega Peptide 7 (SEQ ID NO:7) samples did not show any digestion by Endoprotease Lys C. The lack of digestion of the Promega Peptide 7 (SEQ ID NO:7) by Endoprotease Lys C was expected since no predicted digestion site for the protease was in the peptide.

Example 17

Assays of Proteases in Crude Media Samples

Samples of culture supernate from stationary phase cultures of *Thermus aquaticus* (*T. aquaticus*) and *Brevibacterium albidum* (*B. albidum*) were made by centrifugation of a stationary phase culture at 12,000×g for 2 minutes and transfer of the supernate to fresh tubes. Diluted stocks of Promega Peptides 3 (SEQ ID NO:3), 5 (SEQ ID NO:5) and 6 (SEQ ID NO:6) were made by dilution of the original stocks of these peptides with an equal volume of 50 mM ammonium bicarbonate, pH 7.8. In three independent tubes per peptide, 10 μL of these diluted stocks were incubated with either 10 μL water, 10 μL Thermus supernate, or 10 μL Brevibacterium supernate. The incubations were performed for 90 minutes at 37° C. The samples were then loaded in a 0.9% agarose gel made with 20 mM Tris-Cl pH 8.0. The gel was then electrophoresed at 120 V for 30 minutes, and was photographed under UV light on a transilluminator as described above.

Figure 15:
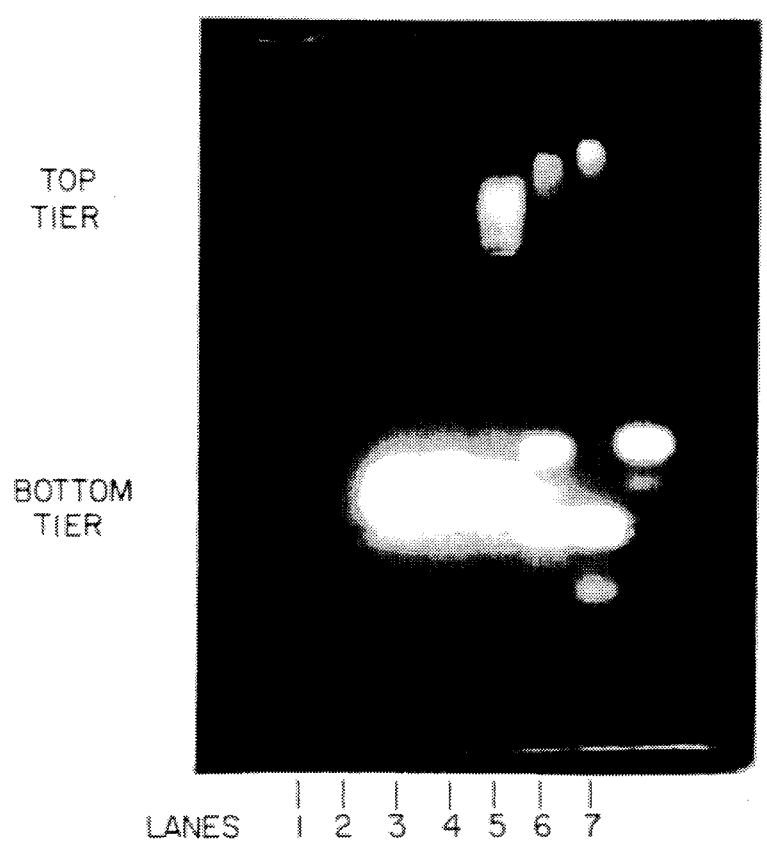
FIG. 15 is a photograph illustrating assays of proteases in crude media samples in Example 17.

Reference is made to FIG. 15, which is a photograph of the agarose gel used to analyze the peptide species produced in the digestion of Promega Peptides 3 (SEQ ID NO:3), 5 (SEQ ID NO:5), and 6 (SEQ ID NO:6) by supernates of cultures of *T. aquaticus* and *B, albidum*. The gel was photographed under UV light as described in Example 1 and the gel is oriented such that the end of the gel which was oriented towards the negative electrode is towards the top of the photograph. The lanes are numbered from left to right:

Lanes 1–4,8 (top tier): blank;

Lane 5 (top tier): sample from the incubation of Promega Peptide 5 (SEQ ID NO:5) with a *B. Albidum* supernate;

Lane 6 (top tier): sample from the incubation of Promega Peptide 5 (SEQ ID NO:5) with a *T. aquaticus* supernate;

Lane 7: control incubation of Promega Peptide 5 (SEQ ID NO:5) without supernate.

The peptide species were produced by incubation of the peptide with the supernates indicating that proteolysis of the peptide had taken place. Lane 1–2 (lower tier): blank;

Lane 3 (lower tier): sample from the incubation of Promega Peptide 3 (SEQ ID NO:3) with supernate from *B. albidum* supernate;

Lane 4 (lower tier): sample of Promega Peptide 3 (SEQ ID NO:3) with supernate from *T. aquaticus* supernate;

Lane 5 (lower tier): sample from a control incubation of Promega Peptide 3 (SEQ ID NO:3) without supernate;

Lane 6 (lower tier): sample of the incubation of Promega Peptide 6 (SEQ ID NO:6) with *B. albidum* supernate;

Lane 7 (lower tier): sample from the incubation of Promega Peptide 6 (SEQ ID NO:6) with *T. aquaticus* supernate;

Lane 8 (lower tier): sample from a control incubation of Promega Peptide 6 (SEQ ID NO:6) without supernate.

The new fluorescent species were observed in lanes 4, 6, and 7, indicating that proteolytic cleavage of the peptide had occurred. Subjecting the gel to prolonged electrophoresis also revealed that the sample in lane 3 did indeed contain a novel peptide species made in small amount which had a slightly faster mobility than the starting peptide.

The gel revealed that new peptide species were generated from the peptides and that the pattern of peptides formed and their amounts were dependent upon the extract used. In addition, the control incubations indicated that the peptides were stable to incubation under these conditions in the absence of protease. Thus these results indicate that such incubations can be used to detect proteases in crude samples and can be used to begin to characterize the types of proteases present in such samples.

Example 18

Quantitation of cAMP-Dependent Protein Kinase Activity Using Microtiter Plate Reader Eight microliters of Promega Peptide 7 (SEQ ID NO:7) was phosphorylated by the catalytic subunit of the cAMP-dependent protein kinase. The amount of kinase used in the assay varied from 4.5 μg to 0.9 ng, diluted from a stock solution of 2.25 mg/ml. The reactions took place in a volume of 24 μl for 30 minutes at room temperature, and were stopped by heating the solutions at 95° C. for five minutes.

After heating, glycerol was added to the solutions to a final concentration of 4%. The solutions were then loaded on a 0.8% agarose gel, which was run at 100 V until the phosphorylated and non-phosphorylated bands had separated and migrated from the wells.

The agarose containing the phosphorylated peptide was excised from the gel with a razor blade and placed into Eppendorph tubes. The agarose was melted, and 145 μl agarose solution were diluted in urea and acetic acid to a final concentration of 2M and 1M, respectively, in a final volume of 250 μl.

The solutions were placed in the wells of a microtiter plate and allowed to cool. After the agarose re-solidified, the absorbance of the wells at 570 nanometers (nm) was read. The results are as listed below in Table 3:

TABLE 3

| # | Dilution | Kinase (μg) | $A_{570}$ | $A_{570}$ - Blank |
|---|---|---|---|---|
| 1–2 | 0 | 0 | 0.097 +/– 0.010 | 0.000 |
| 3–4 | 1:10,000 | 0.0009 | 0.106 +/– 0.013 | 0.009 |
| 5–6 | 1:1,000 | 0.009 | 0.107 +/– 0.003 | 0.010 |
| 7–8 | 1:100 | 0.09 | 0.119 +/– 0.002 | 0.022 |
| 9–10 | 1:10 | 0.9 | 0.204 +/– 0.003 | 0.107 |
| 11–12 | 1:2 | 4.5 | 0.203 +/– 0.005 | 0.106 |

In the range of 0.009 to 0.9 μg kinase added, the correlation coefficient was 0.999, indicating a linear relationship between kinase concentration and absorbance. Under the conditions in which the assay was run, more than 0.9 μg kinase saturated the system, while less than 0.009 μg could not be detected.

Example 19

Quantitation of cAMP-dependent Protein Kinase Activity Using a Spectrophotometer Three microliters of Promega Peptide 7 (SEQ ID NO:7) were phosphorylated by varying amounts of cAMP-dependent protein kinase. The reactions took place in a volume of 20 μl in a solution containing 3 mM ATP, 20 mM HEPES buffer (pH 7.4), and between 50 ng and 1 μg catalytic subunit of cAMP-dependent protein kinase. The mixture was incubated for 30 minutes at room temperature, and the reactions were stopped by heating the mixture at 95° C. for five minutes.

Glycerol was added to a final concentration of 4%, and the mixtures were applied to a 0.8% low melting-point agarose gel (FMC), which was run at 100 V for 10 minutes. At this time, the phosphorylated and non-phosphorylated species had separated and could be detected by ultraviolet light. The phosphorylated peptide was then excised from the gel with a razor blade, and the agarose was melted by heating at 95° C. for 2 minutes. Two hundred microliters of the melted agarose were then diluted to 400 μl in a solution containing 2M urea and 1M acetic acid. The absorbance of the solution at 570 nm was then determined in a Milton-Roy Spectronic 1201 spectrophotometer.

Reference is made to Table 4 as follows for the results:

TABLE 4

| # | Kinase Dilution | Kinase (μg) | $A_{570}$ | $A_{570}$-Blank |
|---|---|---|---|---|
| 1–2 | 0 (blank) | 0 | 0.015 | 0.000 |
| 3–4 | 1:200 | 0.05 | 0.024 | 0.009 |
| 5–6 | 1:100 | 0.10 | 0.036 | 0.021 |
| 7–8 | 1:50 | 0.20 | 0.044 | 0.029 |
| 9–10 | 1:20 | 0.50 | 0.145 | 0.130 |
| 11–12 | 1:10 | 1.0 | 0.178 | 0.163 |

Example 20

Synthesis and Purification of Promega Peptide 7 (SEQ ID NO:7)

A 50 μl solution of Kemptide (Sigma Co.) in 200 mM sodium borate buffer, pH 9.0, was added to 350 μl distilled water. One hundred microliters of acetonitrile containing 10 mg/ml lissamine rhodamine sulfonyl chloride (Molecular Probes) was added. The solution was incubated for 5 minutes, and then agarose gel electrophoresis and visualization of the fluorescent components was performed as described in Example 8.

Figure 16:
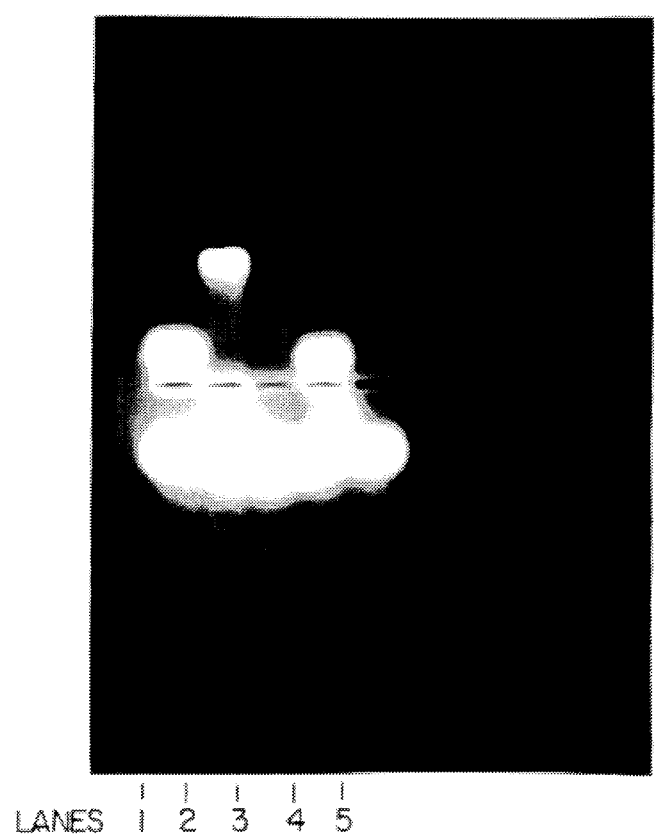
FIG. 16 is a photograph illustrating the quantitation of cAMP-dependent protein kinase activity using a spectrophotometer in Example 20.

Referring the FIG. 16, lane 1, one fluorescent species was found which was migrating towards the positive electrode. This species was identified as Promega Peptide 7 (SEQ ID NO:7). The other lanes were not relevant to this example.

The remaining amount of the synthetic material was applied to a 1 ml bed volume of SP Trisacryl (LKB Corp.) equilibrated with 20 mM ammonium bicarbonate, pH 7.8. The column was washed with 20 mM ammonium bicarbonate, pH 7.8, until the highly colored material which corresponds to the spent derivatizing reagent eluted from the column. One milliliter of 100 mM sodium chloride in 20 mM ammonium bicarbonate, pH 7.8, was then applied to the column followed by several milliliters of 200 mM sodium chloride in 20 mM ammonium bicarbonate, pH 7.8. A colored species eluted from the 200 mM sodium chloride washes which was identified as Promega Peptide 7 (SEQ ID NO:7) by agarose gel electrophoresis as described above. This material was lyophilized to dryness and resuspended in 0.5ml of distilled water to form the solution of Promega Peptide 7 (SEQ ID NO:7).

Example 21

Assay of HIV Protease Using Modified Peptide Substrates

In order to assay the HIV protease using the method employing modified peptide substrates, one of the two following peptides can be dissolved in water to a concentration of 10 mg/ml in water:

PEPTIDE A R-S-L-N-Y-P-Q-S-U-W
PEPTIDE B A-T-L-N-F-P-I-S-P-W

These solutions can be used in synthetic reactions having the following compositions:

10% (v/v) dissolved peptide
10% (v/v) 200 mM sodium borate, pH 9.0

60% (v/v) distilled water
20% (v/v) acetonitrile containing 10 mg/ml lissamine rhodamine sulfonyl chloride (Molecular Probes, Inc.)

The reaction solutions can be incubated at room temperature for 5 minutes following mixing. At this time, the solutions will contain a mixture of highly colored and fluorescent species. These species can be separated and individually visualized by agarose gel electrophoresis as described in many previous examples, such as example 11. The major species will be spent lissamine rhodamine reagent, the other colored species will be the modified peptide desired containing a dye molecule at the amino terminus of the peptide.

Confirmation of the identity of the spent reagent can be done by fractionation of a reaction mixture made as described above, but having the peptide solution added replaced by distilled water. If this is done, the novel colored species observed by electrophoretic fractionation of the sample will be the desired peptide product.

The product from the reaction with peptide A above will generate Promega Peptide 9 (SEQ ID NO:9), which will migrate towards the negative electrode in the gel system described above and which can be purified as described from Promega Peptide 7 (SEQ ID NO:7) presented above.

The product from the reaction with peptide B above will generate Promega Peptide 10 (SEQ ID NO:10), which will migrate towards the positive electrode, but at a slower mobility than that observed for the spent reagent. This modified peptide can be purified as described for Promega Peptide 8 (SEQ ID NO:8), which is presented below.

Example 22

Synthesis and Purification of a Tyrosine Kinase Modified Peptide Substrate, Promega Peptide 8 (SEQ ID NO:8)

The following peptide, a known substrate for the protein tyrosine kinase known as the EGF receptor, was dissolved at a concentration of 10 mg/ml in water:

Asp-Arg-Val-Tyr-Ile-His-Pro-Phe

This peptide was reacted with lissamine rhodamine sulfonyl chloride as described in the previous example. After 20 minutes at room temperature, 5 µl reaction mixture was electrophoresed on a 0.9% agarose gel poured using 20 mM Tris-Cl pH 8.0. The gel was run at 150 V for 30 minutes and was observed and photographed as described in previous examples.

Figure 17:
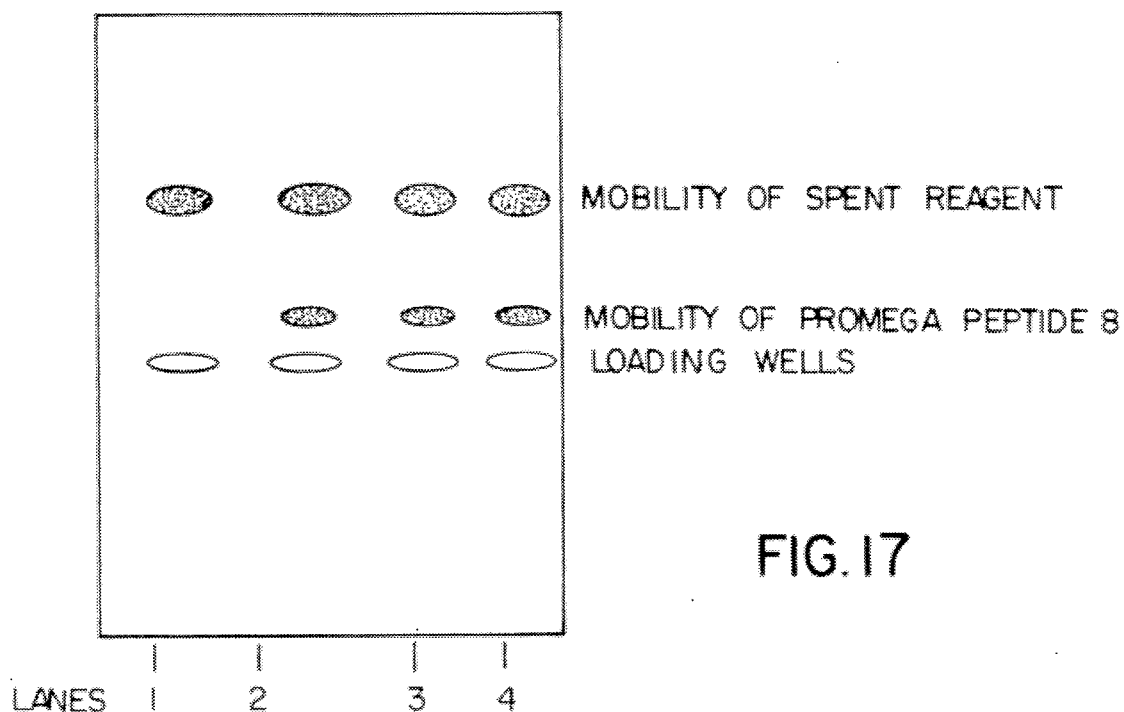
FIG. 17 is a drawing illustrating an agarose gel photograph of the synthesis and purification of a tyrosine kinase modified peptide substrate, Promega Peptide 8 (SEQ ID NO:8) in Example 22.

Reference is made to FIG. 17 for a drawing depicting a gel run for confirmation of the synthesis of Promega Peptide 8 (SEQ ID NO:8), and visualized under UV light. The lanes are numbered from left to right and the gel was run such that the positive electrode was oriented toward the upper segment of the gel, i.e., the upper region of FIG. 17. The samples loaded in the gel were as follows:

Lane 1: control reaction made as described in Example 22 but lacking peptide;

Lanes 2–5: 5 µl samples of the reaction mix made as described in Example 22 which included the peptide.

The new fluorescent species, which was observed in the lanes containing the peptide, had a slower mobility than that of the spent reagent which migrated towards the positive electrode.

Referring to FIG. 17, the photograph revealed that the reactions contained in a fluorescent species that migrated towards the positive electrode which was not present in control reactions made lacking peptide as described in the previous example. This new species had a mobility slower than was seen for the spent reagent which also migrated towards this electrode. This peptide was named Promega Peptide 8 (SEQ ID NO:8).

A 4 ml DEAE sepharose column was poured and equilibrated with 20 mM ammonium bicarbonate, pH 7.8. A 0.5 ml sample of the synthetic mixture was applied to the column, and 5 ml of 20 mM ammonium bicarbonate was applied to the column. Five milliliter fractions were collected throughout the elution and 5ml samples of 30, 40, 50, 75, 100, 150, and 200 mM ammonium bicarbonate, pH 7.8, were applied to the column. After this point, the column was eluted with additional 200 mM ammonium bicarbonate, pH 7.8, and additional 5 ml fractions were collected.

As 200 mM ammonium bicarbonate was applied, two colored species were seen to migrate through the column. The first colored material which eluted was confirmed to be Promega Peptide 8 (SEQ ID NO:8) by agarose gel electrophoresis run as described above. The fractions containing this material were lyophilized and resuspended in 0.5 ml of distilled water to form the pool of Promega Peptide 8 (SEQ ID NO:8). This material can now be used to assay the activity of the EGF Receptor by adding the peptide to a solution of active kinase under conditions where the kinase activity of the enzyme is functional, as is known in the art, and by fractionating the resulting mixture of substrate modified peptide (Promega Peptide 8 (SEQ ID NO:8)) from the product modified peptide by agarose gel electrophoresis as described above, or by use of other separation methods well known in the art and listed above.

If agarose gel electrophoresis is performed, the product modified peptide will migrate towards the positive electrode with a higher mobility than is observed for the substrate modified peptide.

Example 23

Detection of Alkaline Phosphatase Using Non-Radioactive Assay

Promega Peptide 6 (SEQ ID NO:6) was phosphorylated to provide a substrate for alkaline phosphatase in the following manner: 40 µl Promega Peptide 6 (SEQ ID NO:6) were incubated in a solution containing 20 mM HEPES (pH 7.4), 1.67 mM $CaCl_2$, 1 mM dithiothreotol, 10 mM $MgCl_2$, 100 µg/mL phosphatidylserine, 2 mM ATP, and 50 ng protein kinase C in a final volume of 100 µl at 37° C. for 1.5 hours. The reaction was stopped by incubating the mixture at 95° C. for 10 minutes.

After phosphorylation, 0.1M Tris (pH 9.5) was added to a final pH of 9.2. Fifteen microliters of this solution were mixed with between 0.08 to 200 pmoles of alkaline phosphatase in a final volume of 20 µl and incubated at 37° C. for 45 minutes. The reaction was stopped by freezing the mixtures in a dry ice/ethanol bath. Glycerol was added to a final concentration of 4%, and the samples were run on a 0.8% agarose gel at 75 V for 20 minutes. Dephosphorylation of the phosphorylated peptide could be seen with as little as 60 ng added in the dephosphorylation reaction.

Figure 18:
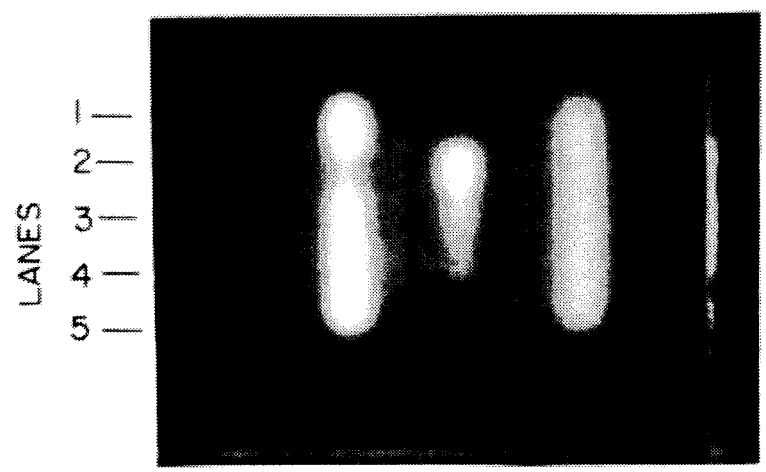
FIG. 18 is a photograph illustrating the detection of alkaline phosphatase using a non-radioactive assay in Example 23.

Reference is made to FIG. 18, which is a photograph of a 0.8% agarose gel depicting the separation of phosphorylated Promega Peptide 1 (SEQ ID NO:1) and Promega Peptide 1 (SEQ ID NO:1) dephosphorylated by alkaline phosphatase as described in this example. The positively charged anode side of the gel is on the right:

Lane 1: 3 µl phosphorylated Promega Peptide 1 (SEQ ID NO:1);

Lane 2: 3 µl phosphorylated Promega Peptide 1 (SEQ ID NO:1) that had not been incubated with Alkaline Phosphatase Lane 3: 3 µl phosphorylated Promega Peptide 1 (SEQ ID NO:1) that had not been incubated with Alkaline Phosphatase 30":

Lane 4: 3 µl phosphorylated Promega Peptide 1 (SEQ ID NO:1) that had not been incubated with Alkaline Phosphatase 5':

Lane 5: 3 µl phosphorylated Promega Peptide 1 (SEQ ID NO:1) that had not been incubated with Alkaline Phosphatase 30'.

Phosphorylated Promega Peptide migrated to the right of the origin; non-phosphorylated peptide migrated to the left. Bands present on the far right are due to free dansyl.

Example 24

Synthesis and Purification of Promega Peptide 11 (SEQ ID NO:11)

A solution of Promega Peptide 6 (SEQ ID NO:6) was diluted with ammonium bicarbonate, pH 7.8, to produce a solution containing 8 mg of peptide in 30 ml of 100 mM ammonium bicarbonate, pH 7.8. To this solution was added 60 µg Endoprotease Lys C (Promega Corp., Madison, Wis.). The solution was incubated at 37° C. for 2 hours.

After this incubation, a second. 60 µg Endoprotease Lys C was added and the solution was allowed to incubate for an additional 2.5 hours. An agarose gel (0.8% agarose in 10 mM Tris pH 8.0) was used to analyze the digest materials.

The gel was electrophoresed as described in Example 16, and the results seen were very similar to the results seen for digestion of Promega Peptide 6 (SEQ ID NO:6) by the protease described in this example where 0.1 µg of protease was used to digest the peptide (see lane 2 of FIG. 13). The peptide species with a mobility approximately 50% of that seen for Promega Peptide 6 (SEQ ID NO:6) is named Promega Peptide 11 (SEQ ID NO:11). Also seen was some material which did not migrate out of the loading wells, this material was not given a Promega Peptide number but is believed to have the sequence Pro-Leu-Ser-Arg and have the Lissamine Rhodamine chemical identification tag present on its amino terminus.

The reaction mixture was diluted to 100 ml with distilled water and applied to a 3 ml column of SP Trisacryl M. The material, which was bound to the column, was washed with 5 ml of 20 mM ammonium bicarbonate, pH 7.8. At this point, 3 ml fractions were first collected and 100 mM ammonium bicarbonate was applied to the column. A colored species began to elute from the column. The colored material which eluted from the column was confirmed to contain Promega Peptide 11 (SEQ ID NO:11) by its mobility on agarose gel electrophoresis as described above. However, some amount of the material which did not migrate from the wells during electrophoresis was also present in the fractions. This material was pooled and lyophilized. The lyophilized fractions were then redissolved in distilled water to produce the pool of Promega Peptide 11 (SEQ ID NO:11).

Figure 19:
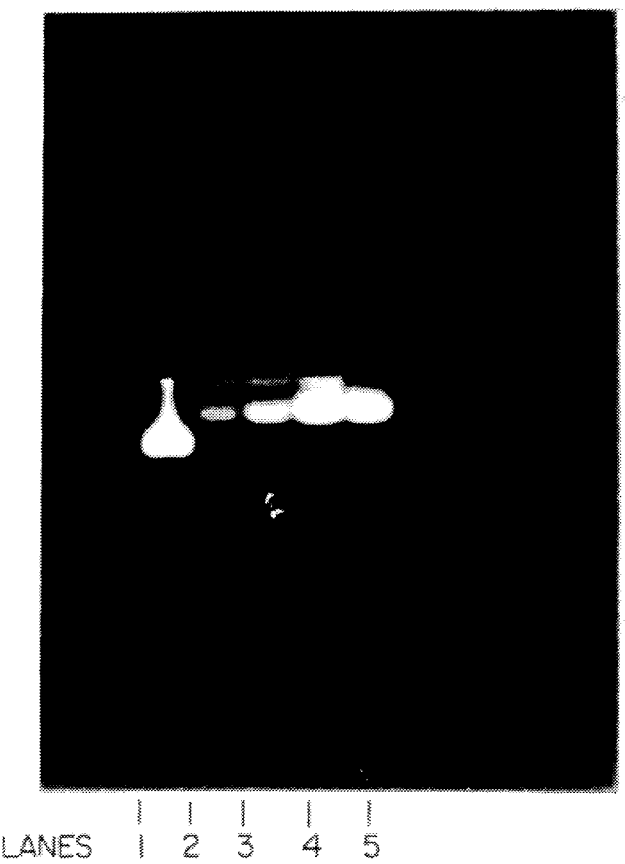
FIG. 19 is a photograph illustrating the synthesis and purification of Promega Peptide 11 (SEQ ID NO:11) in Example 24.

Reference is made to FIG. 19, which is a photograph of the agarose gel used to analyze fractions 1–3 of the SP Trisacryl column. The gel was photographed under UV light as described in Example 1. The gel is oriented such that the end of the gel which was oriented towards the negative electrode is towards the bottom of the photograph. The lanes are numbered from left to right as shown:

Lane 1: sample of undigested Promega Peptide 6 (SEQ ID NO:6) as a mobility control;

Lane 2: sample of the 5 ml, 20 mM ammonium bicarbonate wash (20 µl);

Lanes 3–5: 10 µl sample of fractions 1–3 respectively;

The species migrating with a mobility approximately one-half that seen for Promega Peptide 6 (SEQ ID NO:6) is Promega Peptide 11 (SEQ ID NO:11) and is the major species in lanes 2–5.

Example 25

Detection of Protein Kinase C Activity Using Promega Peptide 11 (SEQ ID NO:11)

One hundred microliters of Promega Peptide 11 (SEQ ID NO:11) were incubated for 2 hours with 20 mM HEPES buffer (pH 7.4), 1.67 mM $CaCl_2$, 200 µg/ml phosphatidyl serine 0.45 mM ATP, 10 mM $MgCl_2$ and 2.5 µg protein kinase C. Reactions were stopped by heating the mixtures to 95° C. for 5 minutes. A 20 µl solution was brought to 4% glycerol and loaded on a 0.8% agarose gel. The gel was run at 100 V for 15 minutes. Phosphorylated Promega Peptide 11 (SEQ ID NO:11) migrated toward the anode, while non-phosphorylated peptide migrated toward the cathode.

Figure 20:
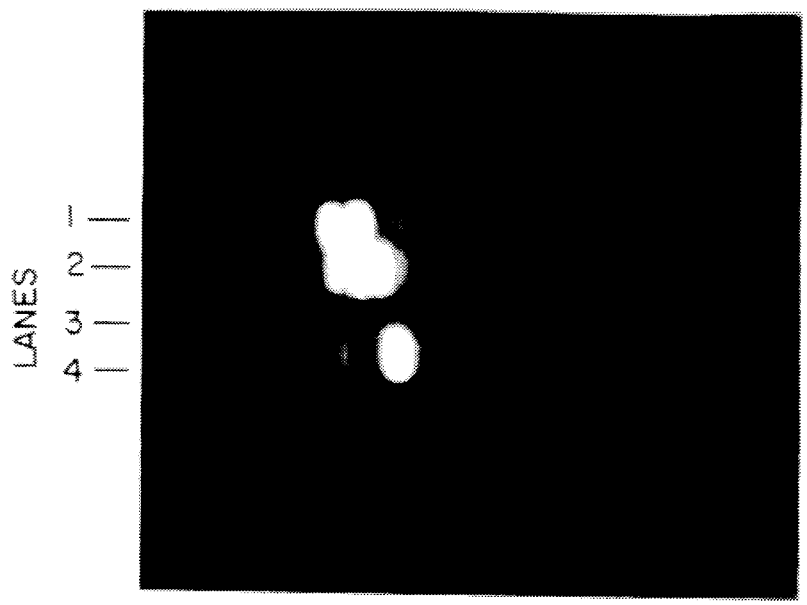
FIG. 20 is a photograph illustrating the detection of protein kinase C activity using Promega Peptide 11 (SEQ ID NO:11) in Example 25.

Reference is made to FIG. 20, which is a photograph of a 0.8% agarose gel used to separate phosphorylated Promega Peptide 11 (SEQ ID NO:11) from the non-phosphorylated species. The gel was run at 100 V for 15 minutes. The positively charged anode is on the right:

Lane 1: 5 µl non-phosphorylated Promega Peptide 11 (SEQ ID NO:11);

Lane 2: 20 µl phosphorylated Promega Peptide 11 (SEQ ID NO:11) (as described in Example 24);

Lane 3: blank;

Lane 4: 5 µl phosphorylated Promega Peptide 7 (SEQ ID NO:7).

It is understood that the invention is not confined to the particular construction and arrangements herein illustrated and described, but embraces such modified forms thereof and come within the scope of the claims following the bibliography.

Bibliography of Cited References

U.S. Pat. No. 5,120,644 to Ikenaka et al.

Bellas, Robert E., Ronit Bendori, Stephen R. Farmer, 1991, "Epidermal Growth Factor Activation of Vinculin and Beta-Integrin Gene Transcription in Quiescent Swiss 3T3 Cells," *J. Biol. Chem.* 266:12008–12014.

Bowen, Heather J., Wiliam J. Enright, Kenji D. Nakamura, 1990, "Synthetic Peptide Substrate Assay for Protein Tyrosine Kinases." *Focus* 12, 4:105–07.

Bramson, H. Neal, Nancy Thomas, William F. DeGrado, E. T. Kaiser, 1980, "Development of a Convenient Spectrophotometric Assay for Peptide Phosphorylation Catalyzed by Adenosine 3', 5'-Monophosphate Dependent Protein Kinase," *J. Amer. Chem. Soc.* 102:7156–7157.

Carr, D. W., S. M. Bishop, T. S. Acott, J. D. Scott, 1991, "Identification and Tissue Distribution of Type I and Type II cAMP-dependent Protein Kinase Anchoring Proteins," Poster #6722, FASEB Conference, Atlanta Ga., 25 April, 1991.

Cook, Paul F., Maynard E. Neville Jr., Kent E. Vrana, F. Thomas Hartl, Robert Roskoski Jr., 1982, "Adenosine Cyclis 3', 5'-Monophosphate Dependent Protein Kinase: Kinetic Mechanism for the Bovine Skeletal Muscle Catalytic Subunit," *Biochemistry* 21:5794–5799.

House, Colin, Richard E. H. Wettenhall, Bruce E. Kemp, 1987, "The Influence of Basic Residues on the Substrate Specificity of Protein Kinase C." *J. Biol. Chem.* 262:772–77.

Hunter, Tony, 1987, "A Thousand and One Protein Kinases," *Cell* 50:823–9.

Kemp, Bruce E. and Richard B. Pearson, 1990, "Protein Kinase Recognition Sequence Motifs," *TIBS* 15:342–346.

Kennelly, Peter J. and Edwin G. Krebs, 1991, "Consensus Sequences as Substrate Specificity Determinants for Protein Kinases and Protein Phosphatases." *J. Biol. Chem.*, 266:15555–15558.

Matthews, H. R., J. Huang, Y. Wei, Y. Kim, 1991, "Protein Histidine Kinase," Poster #2507, FASEB Conference, Atlanta Ga., 23 Apr. 1991.

McMurry, John, 1989, *Essentials of General, Organic, and Biological Chemistry,* Chapter 16: "The Molecules of Life: Enzymes, Vitamins, and Hormones," Prentice-Hall, Inc., New Jersey, pp. 339–359.

Miglietta, Leslie A. P. and David L. Nelson, 1988, "A Novel cGMP-dependent Protein Kinase from Paramecium," *J. Biol. Chem.* 263:16096–16106.

Neurath, H., 1989, "The Diversity of Proteolytic Enzymes," *Proteolytic Enzymes—A Practical Approach,* R. S. Beynor and J. S. Bond (Eds.), I. R. L. Press, Oxford University Press.

Owen, W. G., C. T. Esmon and C. M. Jackson, 1974, *J. Biol. Chem.,* vol. 249, p. 594.

Pawson, Tony and Alan Bernstein, 1990, "Receptor Tyrosine Kinases: Evidence for their Role in Drosophila and Mouse Development," *TIG* 6:350–356.

Pearson, Richard B., James R. Woodgett, Philip Cohen, and Bruce E. Kemp, 1985, "Substrate Specificity of a Multifunctional Calmodulin-dependent Protein Kinase." *J. Biol. Chem.* 260:14471–14476.

Pines, Jonathon and Tony Hunter, 1990, "p34$^{cdc2}$: The S and M Kinase?" *The New Biologist,* 2:389–401.

Rijksen, Gert, Brigit A. van Oirschot, Gerard E. J. Staal, 1989, "A Non-Radioactive Dot-Blot Assay for Protein Tyrosine Kinase Activity." *Anal. Biochem.,* 182–98–102.

Roach, Peter J., 1990, "Control of Glycogen Synthase by Hierarchal Protein Phosphorylation." *The FASB Journal* 4:2961–2967.

Robyt, John F. and Bernard J. White, 1990, *Biochemical Techniques—Theory and Practice,* Waveland Press, Inc., Prospect Heights, Ill., pp. 291–320.

Roskoski, Robert, Jr., 1983, "Assay of Protein Kinases." *Methods in Enzymology,* 99:3–6.

Sarath, G., R. S. de la Motte, and F. W. Wagner, 1989, "Protease Assay Methods," *Proteolytic Enzymes—A Practical Approach,* R. S. Beynor and J. S. Bond (Eds.), I. R. L. Press, Oxford University Press.

Seng, Thomas, Teresa C. M. Eames and David G. Osterman, 1991, "An HPLC Assay for Protein Kinase Activity Using Fluorescence Detection of Dansyl Peptide Substrates," (Abst.) *The Protein Society: Fifth Symposium,* Baltimore, Md., June 22–26, 1991, p. 73.

Todderud, Gordon and Graham Carpenter, 1989, "Epidermal Growth Factor: The Receptor and its Function." *BioFactors* 2:11–15.

Ullrich, Axel and Joseph Schlessinger, 1990, "Signal Transduction by Receptors with Tyrosine Kinase Activity," *Cell* 61:203–212.

Walton, Gordon M., Paul J. Bertics, Laurie G. Hudson, Thomas S. Vedvick and Gordon N. Gill, 1987, "A Three-Step Purification Procedure for Protein Kinase C: Characterization ofthe Purified Enzyme." *Anal. Biochem.* 161:425–437.

---

What is claimed is:

1. A non-radioactive method of quantifying the activity of an enzyme on a peptide substrate, comprising:
   a. adding a sufficient quantity of a substrate modified peptide to the enzyme to produce a product modified peptide wherein the substrate modified peptide includes a detector segment capable of being detected by non-radioactive means for detection;
   b. incubating the enzyme with the substrate modified peptide under conditions where the enzyme is active for a sufficient time to form a product modified peptide;
   c. separating the product modified peptide from the substrate modified peptide by agarose gel electrophoresis; and
   d. measuring the quantity of the product modified peptide by non-radioactive means for detection responsive to the presence of the detector segment.

2. The method of claim 1 wherein the substrate modified peptide is a pure substrate.

3. The method of claim 1 wherein the substrate modified peptide is a crude substrate.

4. The method of claim 1 wherein the substrate modified peptide includes a detector segment selected from the group consisting of dansyl, sulforhodamine, lissamine rhodamine (rhodamine B) and fluorescein.

5. The method of claim 1 wherein the substrate modified peptide is selected from the group consisting of the following peptides: Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 9 (SEQ ID NO:9), Promega Peptide 10 (SEQ ID NO:10), Promega Peptide 11 (SEQ ID NO:11) and analogs thereof.

6. The method of claim 1 wherein the enzyme is selected from the group consisting of kinases, phosphatases and proteases.

7. The method of claim 1 wherein the enzyme is a kinase.

8. The method of claim 7 wherein the substrate modified peptide is selected from the group consisting of Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 11 (SEQ ID NO:11) and analogs thereof.

9. The method of claim 7 wherein the kinase is protein kinase C.

10. The method of claim 9 wherein the substrate modified peptide is selected from the group consisting of Promega Peptide 4 (SEQ ID NO:4), Promega Peptide 5 (SEQ ID NO:5), Promega Peptide 6 (SEQ ID NO:6), Promega Peptide 11 (SEQ ID NO:11) and analogs thereof.

11. The method of claim 7 wherein the enzyme is cAMP-dependent protein kinase.

12. The method of claim 11 wherein the substrate modified peptide is Promega Peptide 1 (SEQ ID NO:1), Promega Peptide 2 (SEQ ID NO:2), Promega Peptide 3 (SEQ ID NO:3), Promega Peptide 7 (SEQ ID NO:7) and analogs thereof.

13. The method of claim 7 wherein the enzyme is tyrosine kinase.

14. The method of claim 13 wherein the substrate modified peptide is Promega Peptide 8 (SEQ ID NO:8) and analogs thereof.

15. The method of claim 1 wherein the enzyme is a phosphatase.

16. The method of claim 15 wherein the substrate modified peptide is selected from the group consisting of Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), [Promega Peptide 9 (SEQ ID NO:9), Promega Peptide 10 (SEQ ID NO:10),] Promega Peptide 11 (SEQ ID NO:11) and analogs thereof, wherein the substrate modified peptide is derived from the products of the reaction of a protein kinase with the substrate modified peptide.

17. The method of claim 15 wherein the enzyme is alkaline phosphatase.

18. The method of claim 1 wherein the enzyme is a protease.

19. The method of claim 18 wherein the substrate modified peptide is selected from the group consisting of Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 9 (SEQ ID NO:9), Promega Peptide 10 (SEQ ID NO:10), Promega Peptide 11 (SEQ ID NO:11) and analogs thereof.

20. The method of claim 18 wherein the enzyme is HIV protease.

21. The method of claim 20 wherein the substrate modified peptide is selected from the group consisting of Promega Peptide 9, (SEQ ID NO:9) and Promega Peptide 10 (SEQ ID NO:10) and analogs thereof.

22. The method of claim 1 wherein the product modified peptide is measured by fluorescence.

23. The method of claim 1 wherein the product modified peptide is measured by chemiluminescence.

24. A method for detecting an enzyme in a body fluid, comprising reacting the body fluid with a sufficient amount of a substrate modified peptide containing a detector segment to enable the enzyme to form a product modified peptide and under conditions where the enzyme is active for a time sufficient to form the product modified peptide in an amount such that the product modified peptide may be detected by non-radioactive means for detection responsive to the detector segment, separating the product modified peptide from the substrate modified peptide by agarose gel electrophoresis, and measuring the amount of product peptide formed using the non-radioactive means for detection.

25. The method of claim 24 wherein the fluid is blood or lymph fluid.

26. The method of claim 24 wherein the substrate modified peptide is selected from the group consisting of the following: Promega Peptide 1 (SEQ ID NO:1), Promega Peptide 2 (SEQ ID NO:2), Promega Peptide 3 (SEQ ID NO:3), Promega Peptide 4 (SEQ ID NO:4), Promega Peptide 5 (SEQ ID NO:5), Promega Peptide 6 (SEQ ID NO:6), Promega Peptide 7 (SEQ ID NO:7), Promega Peptide 8 (SEQ ID NO:8), Promega Peptide 9 (SEQ ID NO:9), Promega Peptide 10 (SEQ ID NO:10), Promega Peptide 11 (SEQ ID NO:11) and analogs thereof.

* * * * *